(12) United States Patent
Catani et al.

(10) Patent No.: US 11,064,942 B1
(45) Date of Patent: Jul. 20, 2021

(54) METHODS AND SYSTEMS TO DETECT EATING

(71) Applicant: OPTUM LABS, LLC, Minneapolis, MN (US)

(72) Inventors: Steven Catani, Athens, GA (US); Jed Ludlow, Draper, UT (US); Tyler Stigen, Minneapolis, MN (US); Joseph A. Roxas, Talisay (PH); Nino Paul D. Batanay, Carmen (PH)

(73) Assignee: OPTUM LABS, LLC, Minneapolis, MN (US)

( * ) Notice: Subject to any disclaimer, the term of this patent is extended or adjusted under 35 U.S.C. 154(b) by 383 days.

(21) Appl. No.: 15/971,835

(22) Filed: May 4, 2018

(51) Int. Cl.
| | |
|---|---|
| G09B 23/28 | (2006.01) |
| A61B 5/00 | (2006.01) |
| A61B 5/145 | (2006.01) |
| A61B 5/11 | (2006.01) |

(Continued)

(52) U.S. Cl.
CPC .......... *A61B 5/4866* (2013.01); *A61B 5/0205* (2013.01); *A61B 5/1123* (2013.01); *A61B 5/14532* (2013.01); *A61B 5/6824* (2013.01); *A61B 5/6825* (2013.01); *A61B 5/7264* (2013.01); *A61B 5/7282* (2013.01); *A61B 5/02416* (2013.01); *A61B 5/02438* (2013.01); *A61B 5/1118* (2013.01); *A61B 2562/0219* (2013.01)

(58) Field of Classification Search
CPC ........... G09B 23/28; A61B 5/02; A61B 5/026; A61B 5/0261; A61B 5/14532
USPC ............. 434/127, 262; 340/539.12; 600/301, 600/309, 365
See application file for complete search history.

(56) References Cited

U.S. PATENT DOCUMENTS

| | | | |
|---|---|---|---|
| 5,398,688 A | * | 3/1995 | Laniado ............ A61B 5/02438 600/437 |
| 6,508,762 B2 | | 1/2003 | Karnieli |
| 6,735,477 B2 | | 5/2004 | Levine |

(Continued)

OTHER PUBLICATIONS

Schianca, Gian Piero Carnevale et al., "The Significance of Impaired Fasting Glucose Versus Impaired Glucose Tolerance," Diabetes Care, vol. 26, No. 5, May 2003, pp. 1333-1337, American Diabetes Association.

(Continued)

*Primary Examiner* — Kurt Fernstrom
(74) *Attorney, Agent, or Firm* — Alston & Bird LLP

(57) ABSTRACT

Embodiments include methods and systems for automated eating detection. Systems comprise a continuous glucose monitor (CGM), accelerometer, and processing unit. During a first time period, the processing unit receives glucose readings and a first set of acceleration readings. The processing unit identifies an eating episode if the glucose readings satisfy one or more criteria. Using the identified eating episode and first set of acceleration readings, the processing unit generates an individual model that identifies eating episodes using acceleration readings without using glucose readings. During a second time period, a processing unit uses the individual model and a second set of acceleration readings to identify a second eating episode. Some embodiments may use additional sensor types (for example, PPG or heart rate) to identify eating episodes in the first or second time period, generate the individual model, or any combination thereof.

11 Claims, 18 Drawing Sheets

(51) Int. Cl.
*A61B 5/0205* (2006.01)
*A61B 5/024* (2006.01)

(56) References Cited

U.S. PATENT DOCUMENTS

| | | | | |
|---|---|---|---|---|
| 8,568,309 | B2 | 10/2013 | Angelides | |
| 8,803,688 | B2* | 8/2014 | Halff | A61B 5/14532 |
| | | | | 340/539.15 |
| 8,870,766 | B2 | 10/2014 | Stivoric et al. | |
| 9,168,000 | B2* | 10/2015 | Dunki-Jacobs | A61B 5/4839 |
| 9,685,097 | B2* | 6/2017 | Hoover | G06K 9/00355 |
| 9,955,914 | B2* | 5/2018 | Dunki-Jacobs | A61B 5/4839 |
| 10,130,277 | B2* | 11/2018 | Connor | A61B 5/7285 |
| 10,314,492 | B2* | 6/2019 | Connor | G09B 19/0092 |
| 10,446,054 | B2* | 10/2019 | Lamoncha | G09B 5/02 |
| 2002/0167863 | A1 | 11/2002 | Davis et al. | |
| 2008/0262745 | A1 | 10/2008 | Polidori | |
| 2009/0177068 | A1 | 7/2009 | Stivoric et al. | |
| 2010/0324432 | A1* | 12/2010 | Bjorling | A61N 1/36007 |
| | | | | 600/504 |
| 2010/0331657 | A1* | 12/2010 | Mensinger | A61B 5/7445 |
| | | | | 600/365 |
| 2011/0021898 | A1 | 1/2011 | Wei et al. | |
| 2011/0270052 | A1 | 11/2011 | Jensen et al. | |
| 2012/0059237 | A1* | 3/2012 | Amir | A61B 5/0285 |
| | | | | 600/365 |
| 2013/0211220 | A1 | 8/2013 | Cobelli et al. | |
| 2014/0005499 | A1 | 1/2014 | Catt et al. | |
| 2015/0045238 | A1 | 2/2015 | Chan et al. | |
| 2015/0217052 | A1 | 8/2015 | Keenan et al. | |
| 2017/0049332 | A1* | 2/2017 | Park | A61B 5/4866 |
| 2017/0164878 | A1* | 6/2017 | Connor | A61B 5/4866 |
| 2017/0249445 | A1* | 8/2017 | Devries | A61B 5/1455 |
| 2018/0277246 | A1* | 9/2018 | Zhong | A61M 5/14212 |
| 2019/0167190 | A1* | 6/2019 | Choi | A61B 5/0261 |
| 2019/0209022 | A1* | 7/2019 | Sobol | H04W 4/38 |
| 2019/0252079 | A1 | 8/2019 | Constantin et al. | |

OTHER PUBLICATIONS

Wikipedia, "Insulin Resistance," Dec. 7, 2016, (17 pages). [Retrieved from the Internet Aug. 22, 2019] <https://en.wikipedia.org/wiki/Insulin_resistance#Fasting_insulin_levels>.

U.S. Patent and Trademark Office, NonFinal Office Action for U.S. Appl. No. 15/372,005, dated Oct. 9, 2019, (26 pages), USA.

Bruno, Barbara; Mastrogiovanni, Fulvio; Sgorbissa, Antonio; Vernazza, Tulio; and Zaccaria, Renato. "Human motion modelling and recognition: A computational approach." Eighth IEEE International Conference on Automation Science and Engineering (CASE), pp. 156-161 (2012).

Bruno, Barbara; Mastrogiovanni, Fulvio; Sgorbissa, Antonio; Vernazza, Tulio; and Zaccaria, Renato. "Analysis of human behavior recognition algorithms based on acceleration data." 2013 IEEE International Conference on Robotics and Automation (ICRA), pp. 1602-1607 (2013).

Chevalier, Guillaume. "LSTMs for Human Activity Recognition." (2016) (https://github.com/guillaume-chevalier/LSTM-Human-Activity-Recognition).

Monte-Moreno, Enric. "Non-invasive estimate of blood glucose and blood pressure from a photoplethysmograph by means of machine learning techniques." Artificial Intelligence in Medicine, 53(2), pp. 127-138 (2011).

Thomaz, Edison; Essa, Irfan; and Abowd, Gregory. "A practical approach for recognizing eating moments with wrist-mounted inertial sensing." Proceedings of the 2015 ACM International Joint Conference on Pervasive and Ubiquitous Computing (UbiComp '15). ACM, New York, NY, USA, pp. 1029-1040 (2015). (https://doi.org/10.1145/2750858.2807545).

NonFinal Office Action for U.S. Appl. No. 16/103,567, dated Feb. 5, 2021, (65 pages), United States Patent and Trademark Office, USA.

* cited by examiner

METHODS AND SYSTEMS TO DETECT EATING

REFERENCE TO TEXT FILE APPENDIX

A computer program listing has been submitted herewith as an ASCII text file and is incorporated by reference in the specification pursuant to MPEP 608.05 I ("Text Files Submitted by EFS-Web"). The name of the ASCII text file is "Appendix_S191V.0020USP_TXT," created on Apr. 23, 2018 with a size of 23 kilobytes.

TECHNICAL FIELD

Present embodiments relate to the use of continuous glucose monitors (CGMs) to detect eating episodes for subsequent use in detecting eating episodes using accelerometer data.

BACKGROUND

Automatically generated data on food consumption has many potential applications. Individuals may be interested in monitoring their own eating behavior for reasons including weight management and control of blood glucose levels. Logging food intake is an established exercise to make individuals more aware of what they eat. However, keeping a written log at the time of food consumption is cumbersome and may often be skipped. Simpler methods, such as taking pictures of foods eaten, may be easily forgotten. Recording food consumption at the end of a day relies on memory, which may be prone to error, particularly with respect to the time at which an individual ate particular foods. In addition, if a food log is used in a coaching program, the coach may not learn about food consumption until long after it has occurred. A system that quickly sends a notification when it detects eating activity would be useful.

Research may seek data with respect to when individuals eat. Some researchers study eating with a focus on the high prevalence of obesity and associated conditions, such as diabetes. Other researchers may focus on eating as a behavior of interest in itself. While a weight loss or glucose management program may seek to make individuals more aware of their eating, some researchers may wish to observe when individuals eat when they are not aware, or have forgotten, that they are being monitored. In such cases, a non-invasive method that attracts little attention from the monitored individual would be ideal. As with other technologies, cost and ease of use are important considerations for creating viable methods. A simple and inexpensive way to detect eating activity would therefore be useful to many.

Existing methods of detecting food consumption include the use of cameras directed towards food to identify food items in the image from the camera. Another visual means uses visual sensors to detect the passage of food through the esophagus. Passage of food through the esophagus may also be determined by ultrasonic sensors that detect changes in esophageal density. Some methods determine eating by analyzing microphone signals for eating sounds. Such methods may employ throat-mounted microphones or be subject to background noise.

One approach seeks to detect eating activity in signals from an accelerometer. This method seeks to detect lulls in activity between peaks attributable to eating activity preparation events or eating activity cleanup events. It does not specify how training data for its detection algorithm would be collected. Further, while it contemplates population-based models whose parameters may be calibrated for an individual subject, it does not disclose models created for an individual from data specific to the individual. Thus, methods and systems collecting training data for eating activity in a simple, automated, and inexpensive way would be useful to the field.

SUMMARY

Embodiments of the present application include methods for automated detection of eating activity. A processing unit receives glucose readings and a first set of acceleration readings generated during a first time period. The glucose readings correspond to glucose levels of an individual and the acceleration readings correspond to motion of either of the individual's hands. The processing unit identifies an eating episode if the glucose readings satisfy one or more criteria. Using one or more identified eating episodes and the acceleration readings, the processing unit then generates an individual model. The individual model identifies eating episodes using acceleration readings but not using glucose readings. A processing unit (either the same processing unit used during the first time period or a second processing unit) uses the individual model and a second set of acceleration readings (generated during a second time period and corresponding to motion of the individual's hand) to identify a second eating episode. Some embodiments may use additional types of data (for example, PPG or heart rate data) to identify eating episodes in the first time period, generate the individual model, identify eating episodes in the second time period, or any combination thereof.

Embodiments include systems for automated eating detection. Systems may include a continuous glucose monitor (CGM), a processing unit, and an accelerometer. The CGM and accelerometer are in communication with the processing unit. The processing unit identifies one or more eating episodes during a first time period using at least the glucose readings generated by the CGM. The processing unit generates an individual model predicting eating episodes using readings from the accelerometer but not using readings from the CGM. The processing unit uses the individual model to identify eating episodes in acceleration readings it receives from the accelerometer during a second time period. Some embodiments may use multiple processing units or multiple accelerometers to perform different steps of the method. Some embodiments may use additional sensor types (for example, PPG or heart rate sensors) to identify eating episodes in the first time period, generate the individual model, identify eating episodes in the second time period, or any combination thereof.

DETAILED DESCRIPTION

Methods

Figure 1:
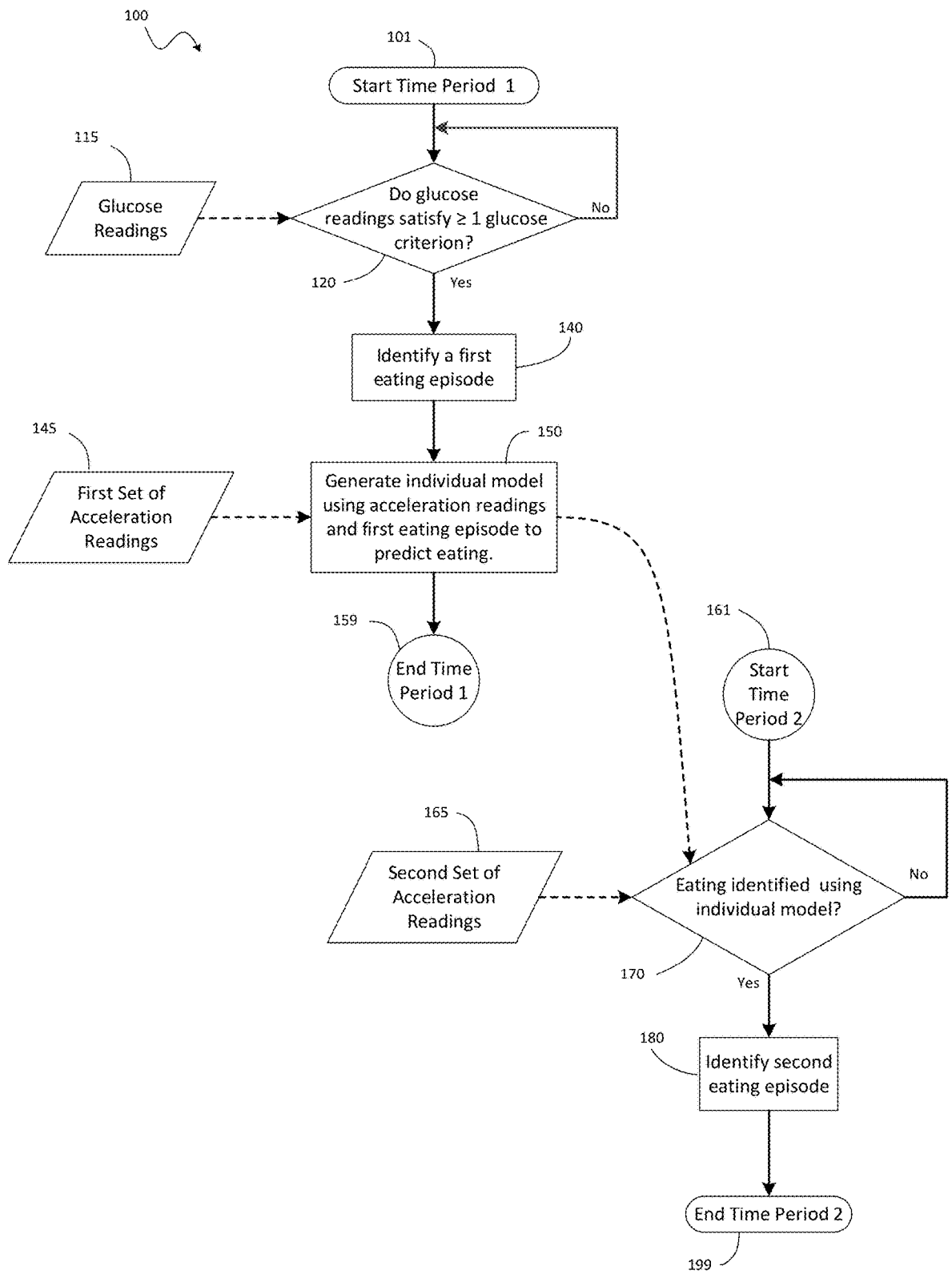
FIG. 1 presents a flowchart illustrating a method for detecting eating activity, according to certain embodiments of the present disclosure.

Embodiments of the present disclosure include methods for detecting eating activity using glucose readings and acceleration readings. A glucose reading may refer to any information or signal that indicates, or may be processed to indicate, a glucose concentration in an individual. Glucose concentrations may be referred to as glucose levels. Glucose readings may be electronic and be either digital or analog in form. Glucose levels may be of the blood, interstitial fluid, or other fluid or tissue of a body. Traditional finger-stick methods measure glucose levels in blood from a puncture wound and provide a glucose reading based on photometric measurement of blood on a test strip. More recently, continuous glucose monitors (CGMs) have been developed to measure glucose levels more frequently than was previously practical. For example, CGM devices may provide glucose readings every five to ten minutes. In addition to a component representing glucose concentration, a glucose reading may also include information as to the time at which the glucose level was measured.

An acceleration reading may refer to any information or signal that indicates, or may be processed to indicate, an amount of acceleration. The acceleration may be linear or angular. An acceleration reading may include information about acceleration along or around more than one axis. For example, a triaxial acceleration reading may indicate acceleration along or around three orthogonal (or approximately orthogonal) axes at a given time. Alternatively, acceleration along or around the three orthogonal axes may be indicated by three separate acceleration readings. In addition to a component representing a quantity of acceleration, an acceleration reading may also include information as to the direction of the acceleration and/or the time at which the acceleration value was generated.

A predictive model (or simply "model") may refer to any algorithm or mathematical expression used to predict a value. A model may predict a future, past, or present state that is not known. Some models are based on statistical methods. Machine learning may incorporate statistical and other mathematical techniques to improve predictions without additional programming. Machine learning may be supervised or unsupervised. Unsupervised techniques start with no examples outputs assigned to inputs. Supervised techniques seek to determine rules that provide correct outputs based on inputs. Supervised techniques require a training data set (a set of example inputs each paired with a desired output) from which to learn.

Supervised machine learning techniques may be used to predict eating activity provided an adequate training data set. Collecting adequate training data has proven to be a challenge. Methods requiring an observer recording onset and end of eating activity may be expensive and arduous even to obtain small quantities of data. Requiring individuals to record their own eating activity is problematic for reasons noted above. Data from CGMs may be used as an indicator of eating activity and used to generate training data to detect eating activity using other sensor types. However, CGM devices currently cost more than other types of biosensors and using CGMs for long term monitoring may be prohibitively expensive. Additionally, using devices less invasive than CGMs may also be more practical to detect eating activity over longer time periods due to higher utilization compliance by monitored individuals. It may therefore be advantageous to use CGMs for a limited time to collect training data to create models allowing other types of biosensors to detect eating activity.

When training data on eating activity can be efficiently collected in large enough quantities, creating training data sets specific to individuals (rather than populations) becomes feasible. Preferred embodiments of the present disclosure generate models based on CGM training data specific to a single individual to identify patterns of eating activity specific to that individual.

A computer processing unit (or, simply "processing unit") may comprise one or more computer processors and any memory necessary to process data. If a processing unit comprises multiple processors, those processors may or may not be locate in close physical proximity. A processing unit may receive glucose readings generated by a CGM or other glucose sensor. The processing unit may identify an episode of eating activity when one or more glucose readings satisfy one or more glucose criteria. Examples of glucose criteria include: (1) at least one of the glucose readings exceeding a threshold glucose level; (2) a rate of glucose change exceeding a threshold rate of glucose change; or (3) a derivative of the rate of glucose change exceeding a threshold for the derivative of the rate of glucose change. The one or more glucose criteria may include criteria as to time, duration, and other contemporaneous conditions.

Once the processing unit has identified one or more eating episodes, it may then apply various machine learning or other modeling techniques to identify patterns in data from a second sensor that are predictive of the one or more eating episodes. Accelerometers are a second sensor in preferred embodiments. Once the processing unit generates an individual model of eating movement, it, or another processing unit, may then identify one or more eating episodes using acceleration readings without using glucose readings as an input.

FIG. 1 presents a flowchart illustrating a method (100) for detecting eating activity, according to certain embodiments of the present disclosure. After the start of a first time period (101), a processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit identifies a first eating episode (140). Using a first set of acceleration readings (145) generated during the first time period, the processing unit generates an individual model predicting eating episodes using at least the first eating episode as training data (150). The individual model predicts eating episodes using acceleration readings. Those familiar with the art will understand that multiple identified eating episodes in addition to the first eating episode may be used as training data to generate the individual model. The individual model may become more robust as more identified eating episodes are included in the training data set. Collection of training data ceases at the end of the first time period (159). A second time period begins at 161. A processing unit (either the same used in the first time period or a second processing unit) applies the individual model generated at 150 to a second set of acceleration readings (165) generated during the second time period to determine whether eating activity is occurring (170). If the individual model indicates no activity, processing repeats step 170 to monitor subsequent acceleration readings for eating activity. If eating activity is detected, the processing unit identifies a second eating episode (180) and ends (199).

Not all accelerometer data is equally predictive. Most individuals eat using their hands (e.g. to manipulate utensils for eating). Some embodiments place the accelerometer at a body location whose movement is indicative of movement of one of the individual's hands, particularly the individual's dominant hand or the hand the individual typically uses to eat. For example, the accelerometer may be coupled the wrist, forearm, or hand itself.

Figure 2:
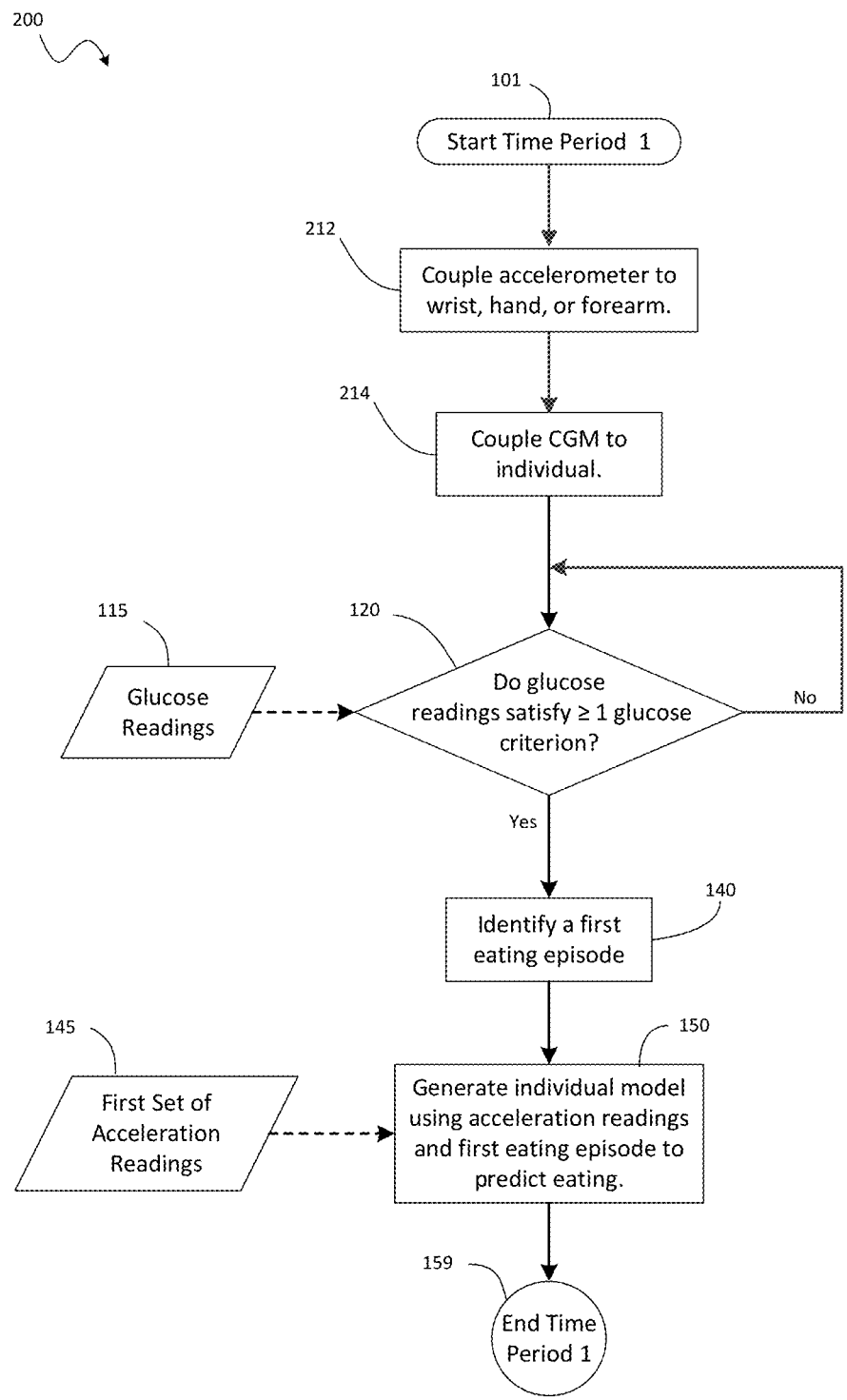
FIG. 2 presents a flowchart illustrating a method for detecting eating activity including steps of coupling a CGM and an accelerometer to an individual, according to certain embodiments of the present disclosure.

FIG. 2 presents a flowchart illustrating a method (200) for detecting eating activity including steps of coupling a CGM and an accelerometer to an individual, according to certain embodiments of the present disclosure. A first time period begins at 101. An accelerometer is coupled to a wrist, hand, or forearm of an individual (212). Preferred embodiments may couple the accelerometer to the individual's dominant side or the side the individual typically uses to eat. A CGM is coupled to the individual allowing the CGM to generate glucose readings corresponding to glucose levels of the individual (214). A processing unit then determines whether the glucose readings (115) generated by the CGM during the first time period satisfy one or more glucose criteria (120). If not, processing repeats step 120 to determine whether subsequent glucose readings satisfy the one or more glucose criteria. If the glucose readings satisfy the one or more glucose criteria, the processing unit identifies a first eating episode (140). Using a first set of acceleration readings (145) generated during the first time period, the processing unit generates an individual model predicting eating episodes using at least the first eating episode as training data (150). The individual model identifies eating episodes in acceleration readings. Collection of training data ceases at the end of the first time period (159). The individual model may then be used to identify eating episodes using acceleration readings during a second time period, as described in FIG. 1 and elsewhere herein.

Figure 3:
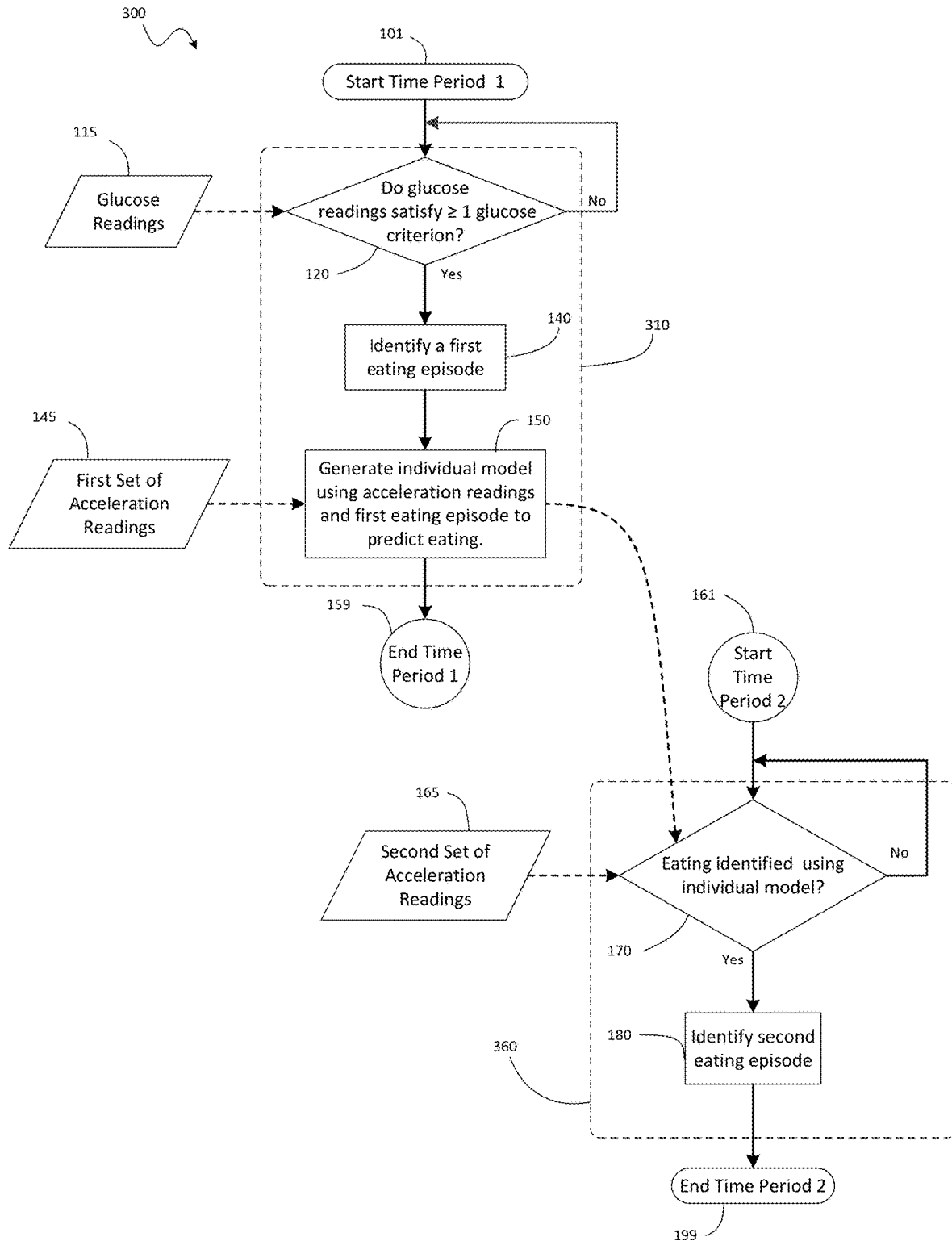
FIG. 3 presents a flowchart illustrating a method for detecting eating activity using first and second processing units, according to certain embodiments of the present disclosure.

FIG. 3 presents a flowchart illustrating a method (300) for detecting eating activity using first and second processing units, according to certain embodiments of the present disclosure. The steps of FIG. 3 are the same as those in FIG. 1. Steps 120 (determining whether glucose readings satisfy one or more criteria), 140 (identifying a first eating episode), and 150 (generating an individual model) are performed at a first processing unit (310). Steps 170 (identifying eating using the individual model) and 180 (identifying a second eating episode) are performed on a second processing unit (360). Those familiar with the art will understand that the steps of the method (300) could each be performed by a single processing unit or that multiple processing units could perform any combination of the steps. For example, identifying the first eating episode (140) could be performed by a different processing unit than the step of generating the individual model (150). Given that a processing unit may comprise more than one processor and that multiple processors within a processing unit need not be located in close proximity with one another, distinctions among which steps are performed by which processors are largely immaterial in the context of the method.

Figure 4:
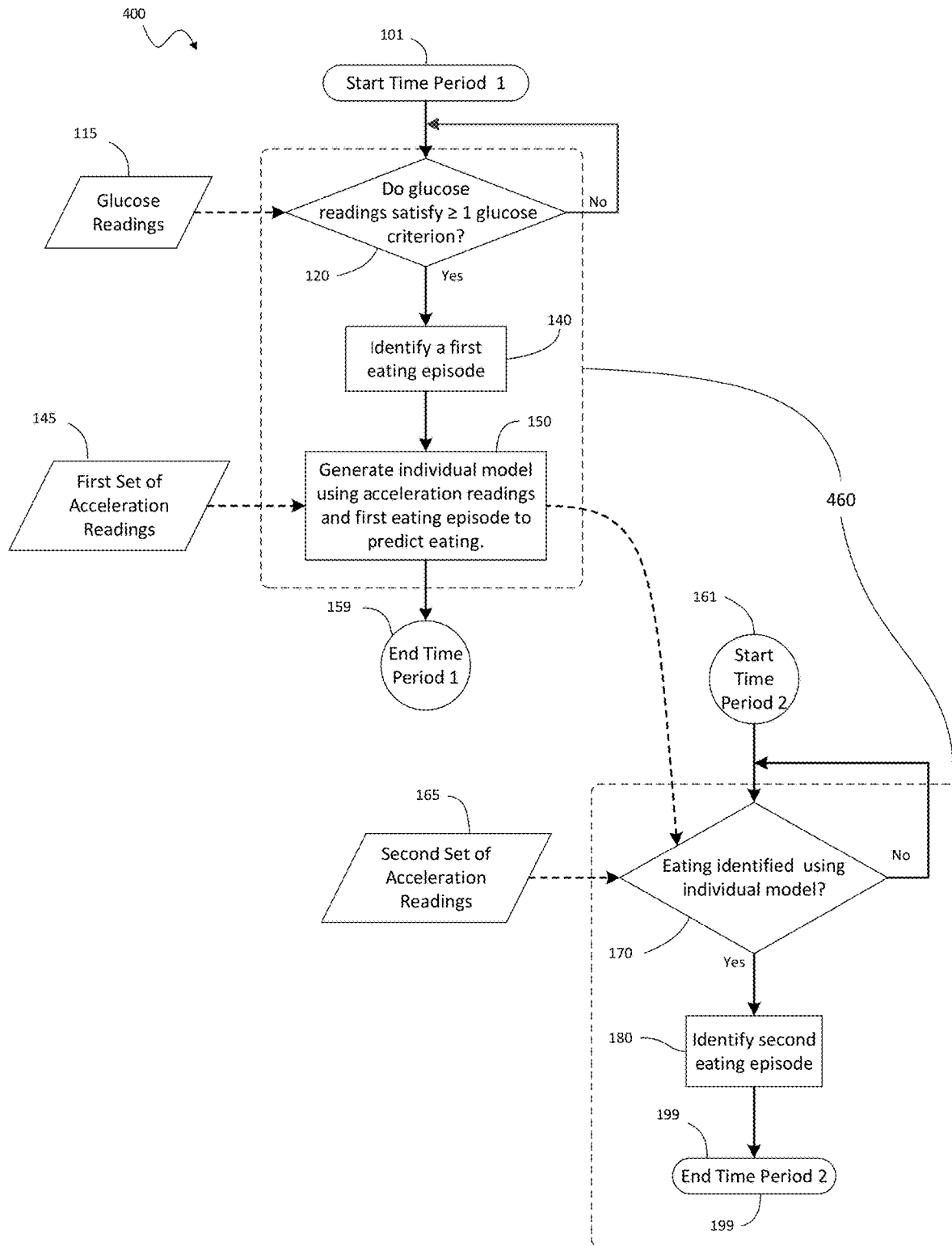
FIG. 4 presents a flowchart illustrating a method for detecting eating activity using a single processing unit, according to certain embodiments of the present disclosure.

FIG. 4 presents a flowchart illustrating a method (400) for detecting eating activity using a single processing unit, according to certain embodiments of the present disclosure. FIG. 4 is identical to FIG. 3 except that all steps are performed by a single processing unit (460). Again, this figure illustrates that distinctions among which steps are performed by which processors are largely immaterial in the context of the method.

Eating is not the only activity that can cause glucose levels to increase. For example, gluconeogenesis (a physiological process in which glucose may be synthesized from lipids or proteins) can cause glucose levels to increase. Breakdown of glycogen can also increase glucose levels. How can increases in glucose levels caused by eating activity be distinguished from other causes? Glucose signals showing increases caused by eating may have different characteristics than those with other causes. In this case, eating may still be determined from glucose readings alone. Alternatively, input from a second sensor may help distinguish eating activity from other glucose increases. Population-based models of eating movement provide one means for distinguishing eating activity. Such population-based models may be applied to acceleration data to determine potential eating episodes. If an increase in glucose levels occurs within a short time of when a population-based model indicates a potential eating episode, it may be reasonable to infer that eating activity caused the glucose increase. However, if no eating motions occur near the time of glucose increase, the increase may be due to non-eating factors. This may especially be the case when non-eating motion patterns, such as physical exercise, are identified in acceleration readings. Conversely, identification by the population-based model of a potential eating episode that is not accompanied by an increase in glucose may be caused by motions that are not associated with eating. The population-based model may be used to identify eating episodes in training data so that an individual (non-population-based) model may be generated for use after the training period.

Figure 5:
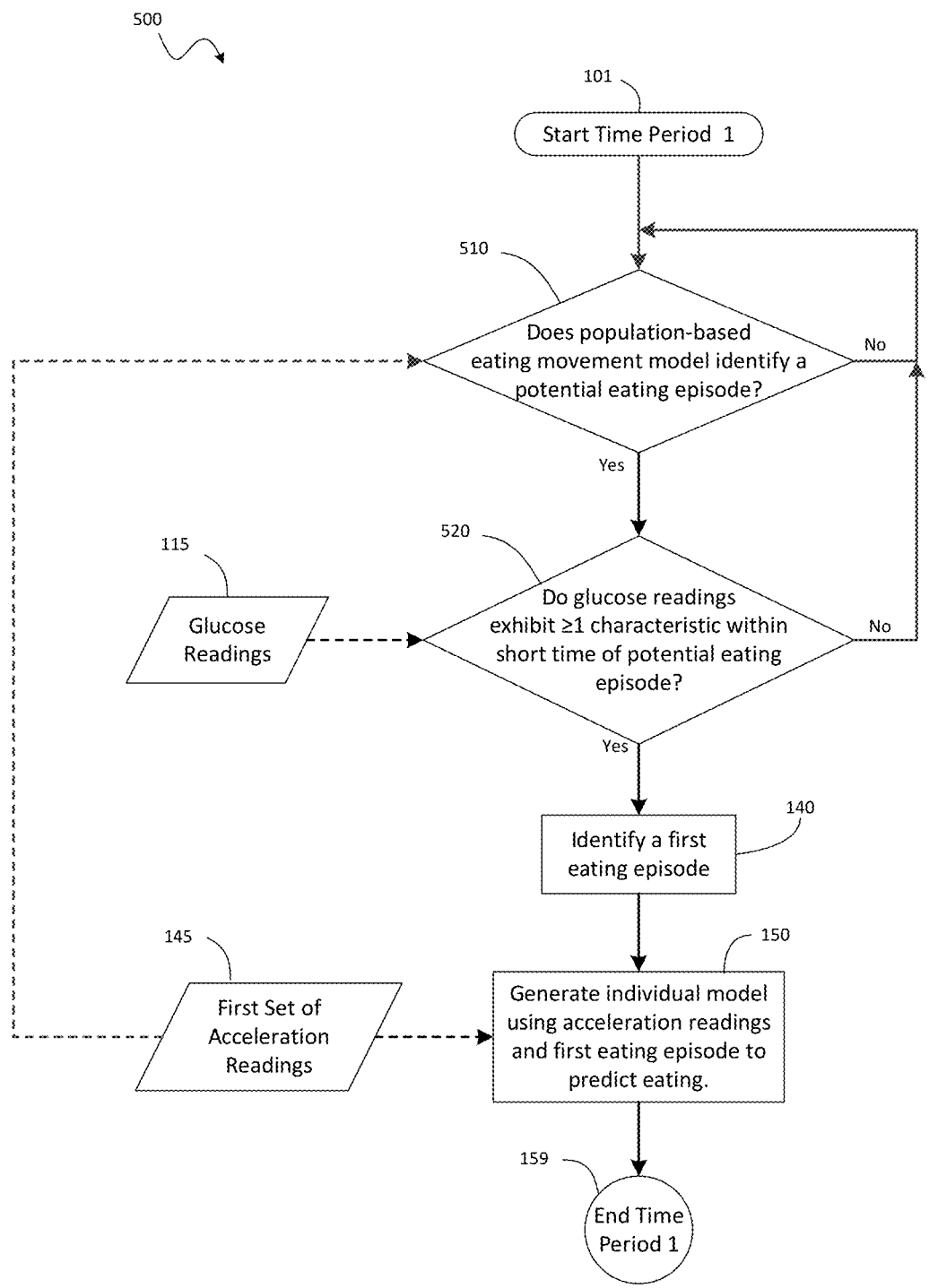
FIG. 5 presents a flowchart illustrating a method for detecting eating activity using a population-based eating movement model and glucose readings to identify a first eating episode, according to certain embodiments of the present disclosure.

FIG. 5 presents a flowchart illustrating a method (500) for detecting eating activity using a population-based eating movement model and glucose readings to identify a first eating episode, according to certain embodiments of the present disclosure. A first time period begins at 101. A processing unit applies a population-based eating movement model to a first set of acceleration readings (145) to determine whether there is a potential eating episode (510). If not, processing repeats step 510 to determine whether subsequent acceleration readings indicate a potential eating episode according to the population-based model. If the population-based model indicates a potential eating episode, the processing unit then determines whether the glucose readings (115) generated during the first time period satisfy one or more glucose criteria within a threshold amount of time from the potential eating episode (520). If not, processing returns to step 510 to determine whether subsequent acceleration readings indicate a potential eating episode according to the population-based model. If the glucose readings satisfy the one or more glucose criteria within the threshold amount of time, the processing unit identifies a first eating episode (140). Using the first set of acceleration readings (145) generated during the first time period, the processing unit generates an individual model predicting eating episodes using at least the first eating episode as training data (150). The individual model identifies eating episodes using acceleration readings. Collection of training data ceases at the end of the first time period (159). The individual model may then be used to identify eating episodes using acceleration readings during a second time period, as described in FIG. 1 and elsewhere herein.

A photo-plethysmograph (PPG) is a second sensor type that may be used to identify eating episodes. While plethysmography refers generally to the measurement of volume, PPG has many applications beyond volume measurements. PPG devices measure either absorbance or transmission of light, especially light in the infrared (IR) part of the spectrum. Because blood absorbs IR light to a greater degree than other tissues, the intensity of absorbed or transmitted IR light may be proportional to the amount of blood in blood vessels, especially the capillaries and other microvascular tissue. This proportionality may be distinguished from an absolute volume measurement. Rapid changes in IR absorbance may be attributed to blood volume changes caused by heart beats. In addition to measuring blood flow, PPG may be used to measure blood oxygen saturation due to the difference in IR absorbance between oxygenated and non-oxygenated blood. PPG may be used to determine other physiological measures as well. Thus, as used herein, a PPG reading may refer to any measurement of light absorbance or transmission from a body or to any particular measure derived from changes in absorbance or transmission.

PPG readings may be used to increase predictive accuracy at various points in the method. For example, PPG readings may be used in addition to glucose readings to identify one or more eating episodes for a training data set. PPG readings may be used in addition to acceleration readings generated in a training period to generate an individual model. PPG may also be used in addition to acceleration readings to identify eating episodes after the training period has ended. These scenarios are illustrated in the next three figures.

Figure 6:
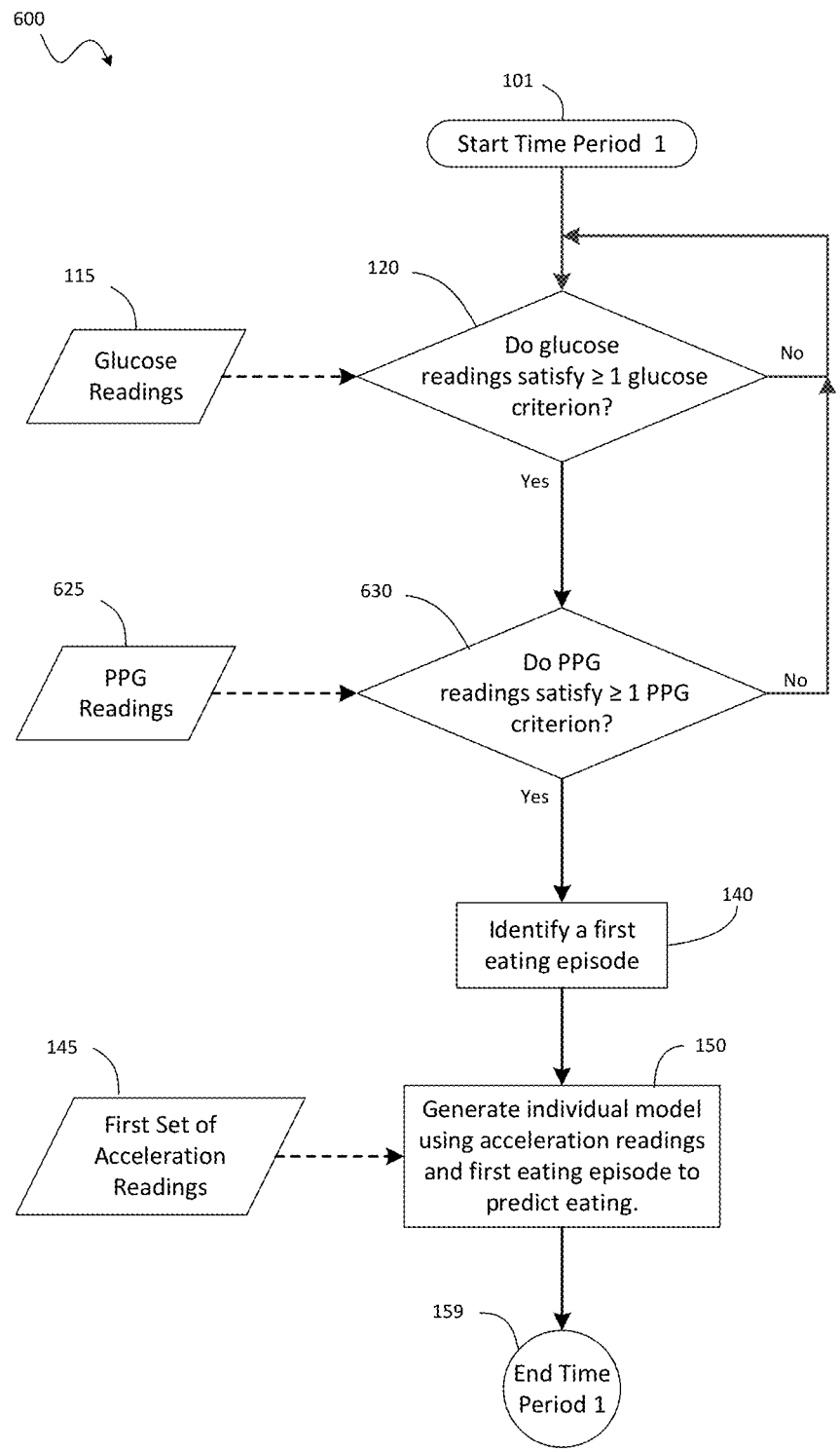
FIG. 6 presents a flowchart illustrating a method for detecting eating activity using glucose readings and PPG readings to determine a first eating episode, according to certain embodiments of the present disclosure.

FIG. 6 presents a flowchart illustrating a method (600) for detecting eating activity using glucose readings and PPG readings to determine a first eating episode, according to certain embodiments of the present disclosure. After the start of a first time period (101), a processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit determines whether PPG readings (625) generated during the first time period satisfy one or more PPG criteria (630). If not, processing returns to step 120 to determine whether glucose readings satisfy the one or more glucose criteria. If the PPG readings satisfy the one or more PPG criteria, the processing unit identifies a first eating episode (140). Using a first set of acceleration readings (145) generated during the first time period, the processing unit generates an individual model predicting eating episodes using at least the first eating episode as training data (150). The individual model identifies eating episodes in acceleration readings. Collection of training data ceases at the end of the first time period (159). The individual model may then be used to identify eating episodes using acceleration readings during a second time period, as described in FIG. 1 and elsewhere herein.

Figure 7:
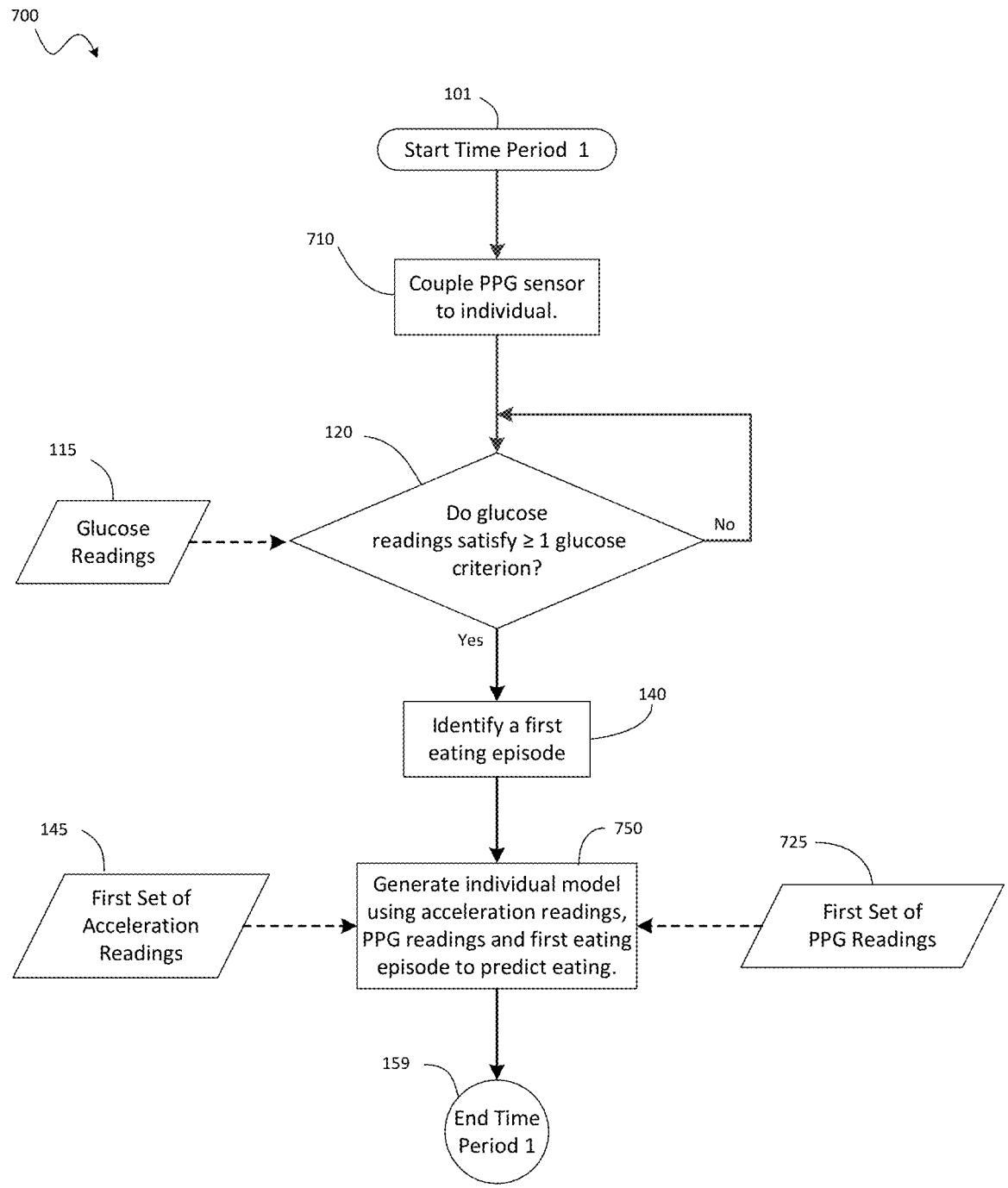
FIG. 7 presents a flowchart illustrating a method for detecting eating activity using acceleration readings and PPG readings to generate an individual eating model, according to certain embodiments of the present disclosure.

FIG. 7 presents a flowchart illustrating a method (700) for detecting eating activity using acceleration readings and PPG readings to generate an individual eating model, according to certain embodiments of the present disclosure. After the start of a first time period (101), a PPG sensor is coupled to an individual such that it measures PPG readings from some part of the individual's body (710). A processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit identifies a first eating episode (140). Using a first set of acceleration readings (145) and a first set of PPG readings (725), both sets of readings generated during the first time period, the processing unit generates an individual model predicting eating episodes using at least the first eating episode (750). The individual model predicts eating episodes using acceleration readings and PPG readings. Collection of training data ceases at the end of the first time period (159). The individual model may then be used to identify eating episodes using acceleration readings and PPG readings during a second time period, as described in, for example, FIG. 8 and elsewhere herein.

Figure 8:
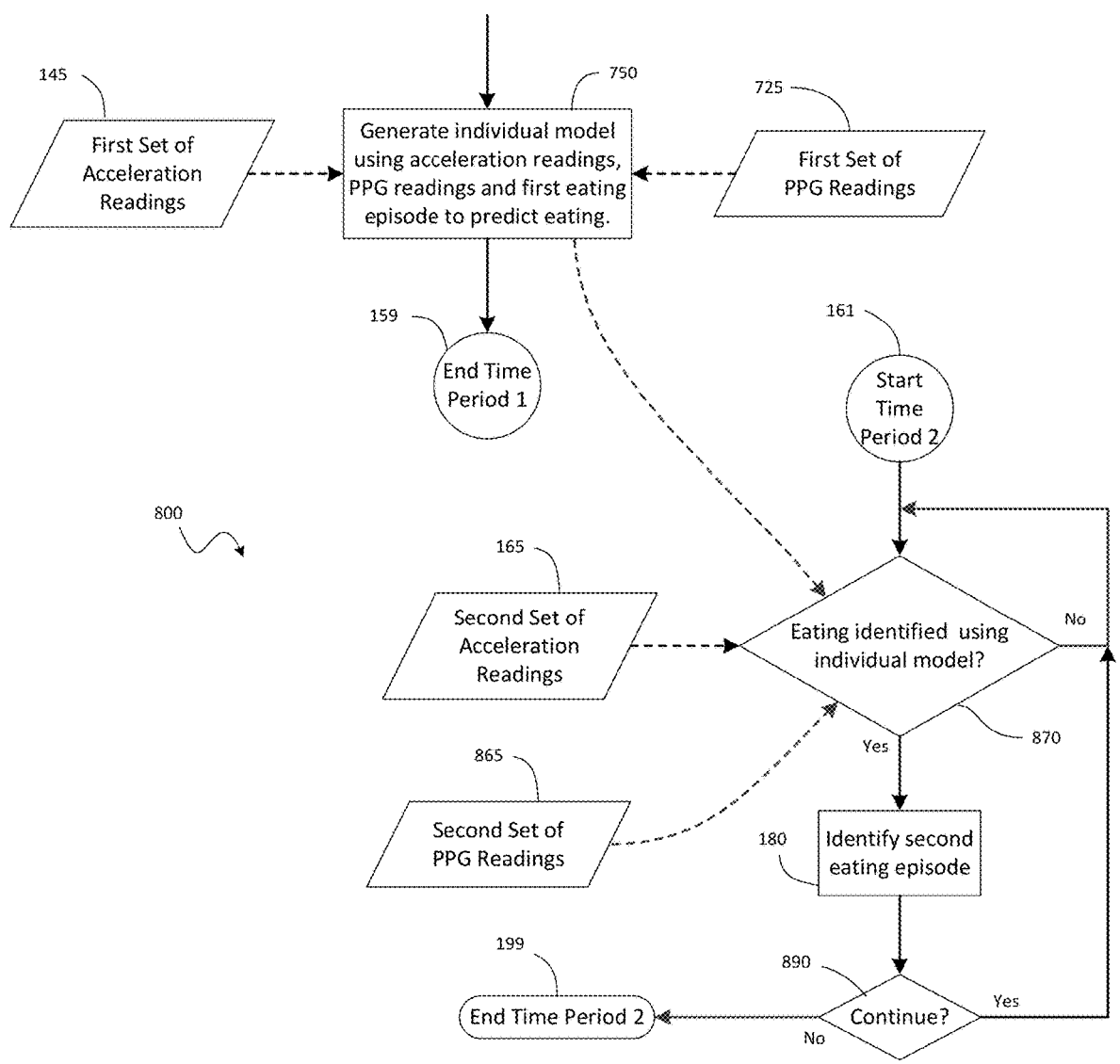
FIG. 8 presents a flowchart illustrating a method for detecting eating activity using acceleration readings and PPG readings to identify a second eating episode, according to certain embodiments of the present disclosure.

FIG. 8 presents a flowchart illustrating a method (800) for detecting eating activity using acceleration readings and PPG readings to identify a second eating episode, according to certain embodiments of the present disclosure. Method 800 begins after creation of an individual model predicting eating episodes using acceleration readings and PPG readings as, for example, in FIG. 7. A second time period begins at 161. A processing unit (either the same used in the first time period or a second processing unit) applies an individual model to a second set of acceleration readings (165) and a second set of PPG readings (865), both sets of readings generated during the second time period, to determine whether there is eating activity (870). If the individual model indicates no activity, processing repeats step 870 to monitor acceleration readings and PPG readings for eating activity. If eating activity is detected, the processing unit identifies a second eating episode (180). Processing then determines whether to continue monitoring for additional eating episodes (890). If additional monitoring is indicated, processing returns to step 870. If no further monitoring occurs, the method (800) ends (199).

A heart rate sensor may refer to any device or component that detects heart beats. Two types of sensor are commonly used. One is PPG, which detects light transmission or absorbance, as discussed herein. Electrocardiography (ECG) is another method of detecting heart beats. ECG detects electrical pulses from the cells that initiate heart beats. The electrical pulses are detected by electrodes which may contact the skin. Electrodes placed directly over the heart may receive the strongest electrical activity, but electrodes at more remote locations (e.g. wrist, hands, or fingers) may be able to detect cardiac electrical activity. A heart rate reading may refer to any output of a heart rate sensor. A heart rate reading may correspond to a single heart beat or a multiple heart beats. A heart rate reading may correspond to a period of time in which no heart beats are detected. A heart rate reading may be digital or analog and correspond either some count of heart beats or some output from which a count of heart beats may be derived.

Figure 9:
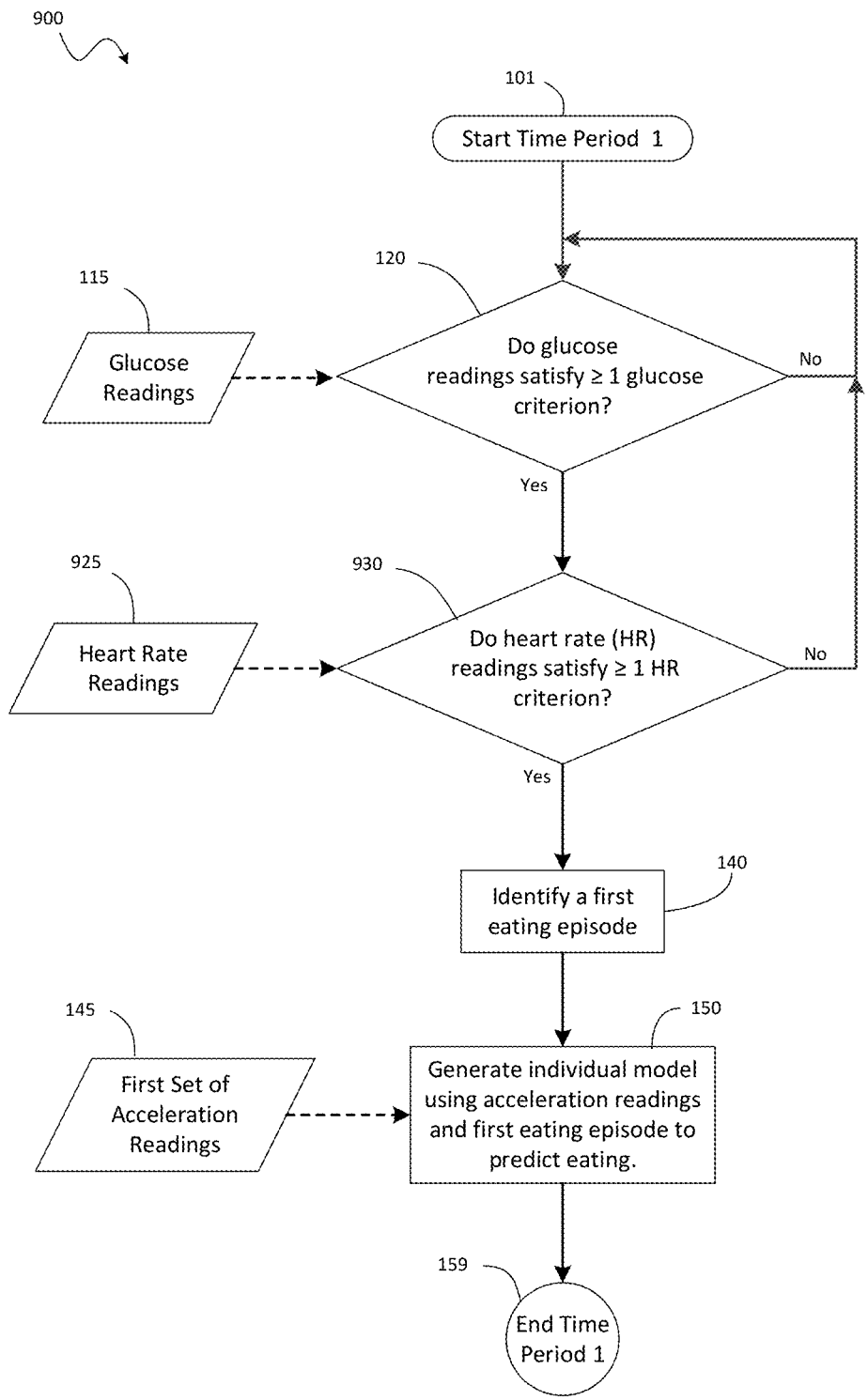
FIG. 9 presents a flowchart illustrating a method for detecting eating activity using glucose readings and heart rate readings to determine a first eating episode, according to certain embodiments of the present disclosure.

FIG. 9 presents a flowchart illustrating a method (900) for detecting eating activity using glucose readings and PPG readings to determine a first eating episode, according to certain embodiments of the present disclosure. After the start of a first time period (101), a processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit determines whether heart rate readings (925) generated during the first time period satisfy one or more heart rate criteria (930). If not, processing returns to step 120 to determine whether glucose readings satisfy the one or more glucose criteria. If the heart rate readings satisfy the one or more heart rate criteria, the processing unit identifies a first eating episode (140). Using a first set of acceleration readings (145) generated during the first time period, the processing unit generates an individual model predicting eating episodes using at least the first eating episode as training data (150). The individual model identifies eating episodes using acceleration readings. Collection of training data ceases at the end of the first time period (159). The individual model may then be used to identify eating episodes using acceleration readings during a second time period, as described in FIG. 1 and elsewhere herein.

Figure 10:
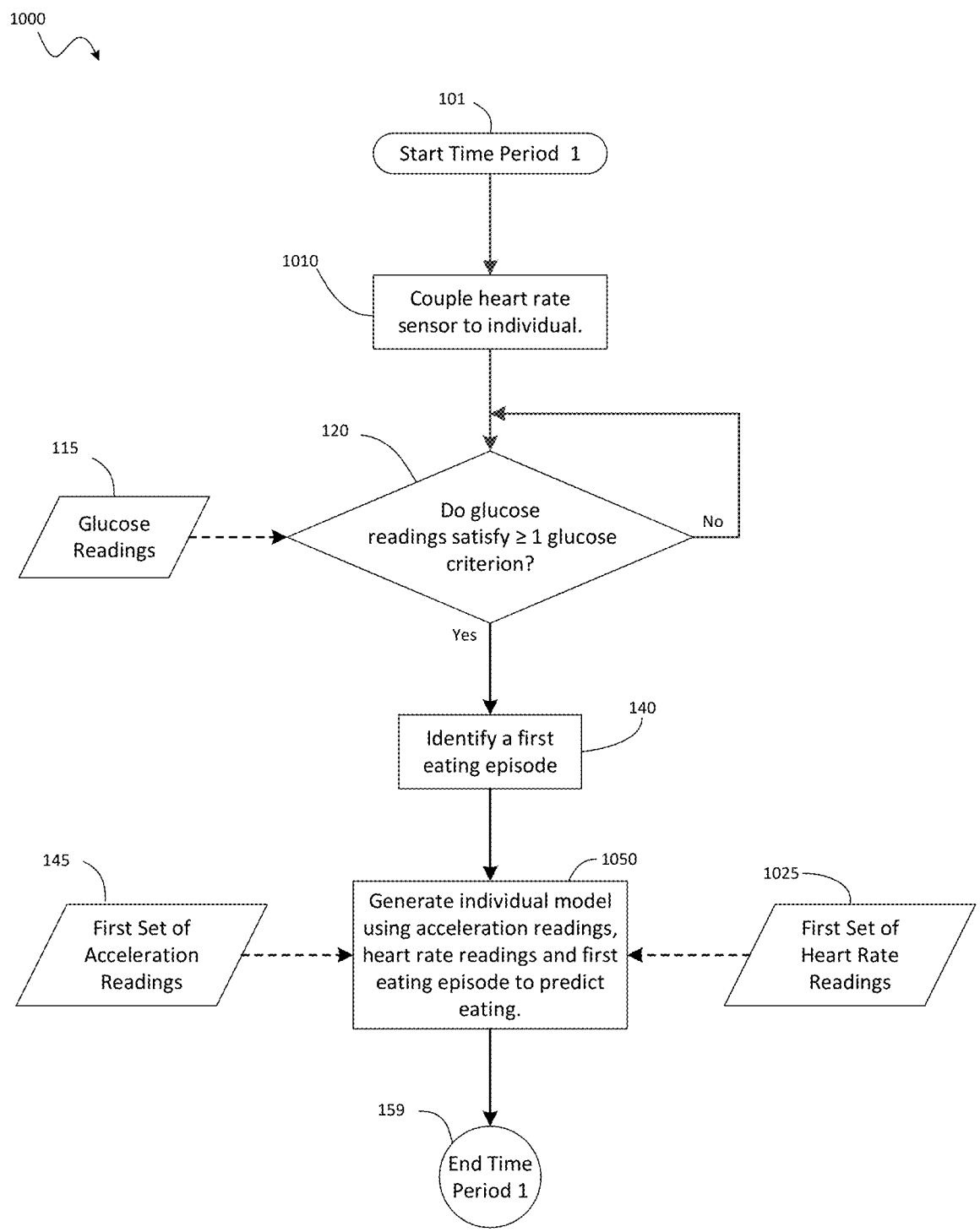
FIG. 10 presents a flowchart illustrating a method for detecting eating activity using acceleration readings and heart rate readings to generate an individual eating model, according to certain embodiments of the present disclosure.

FIG. 10 presents a flowchart illustrating a method (1000) for detecting eating activity using acceleration readings and heart rate readings to generate an individual eating model, according to certain embodiments of the present disclosure. After the start of a first time period (101), a heart rate sensor is coupled to an individual (1010). A processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit identifies a first eating episode (140). Using a first set of acceleration readings (145) and a first set of heart rate readings (1025), both sets of readings generated during the first time period, the processing unit generates an individual model predicting eating episodes using at least the first eating episode as training data (1050). The individual model predicts eating episodes using acceleration readings and heart rate readings. Collection of training data ceases at the end of the first time period (159). The individual model may then be used to identify eating episodes using acceleration readings and heart rate readings during a second time period, as described in, for example, FIG. 11 and elsewhere herein.

Figure 11:
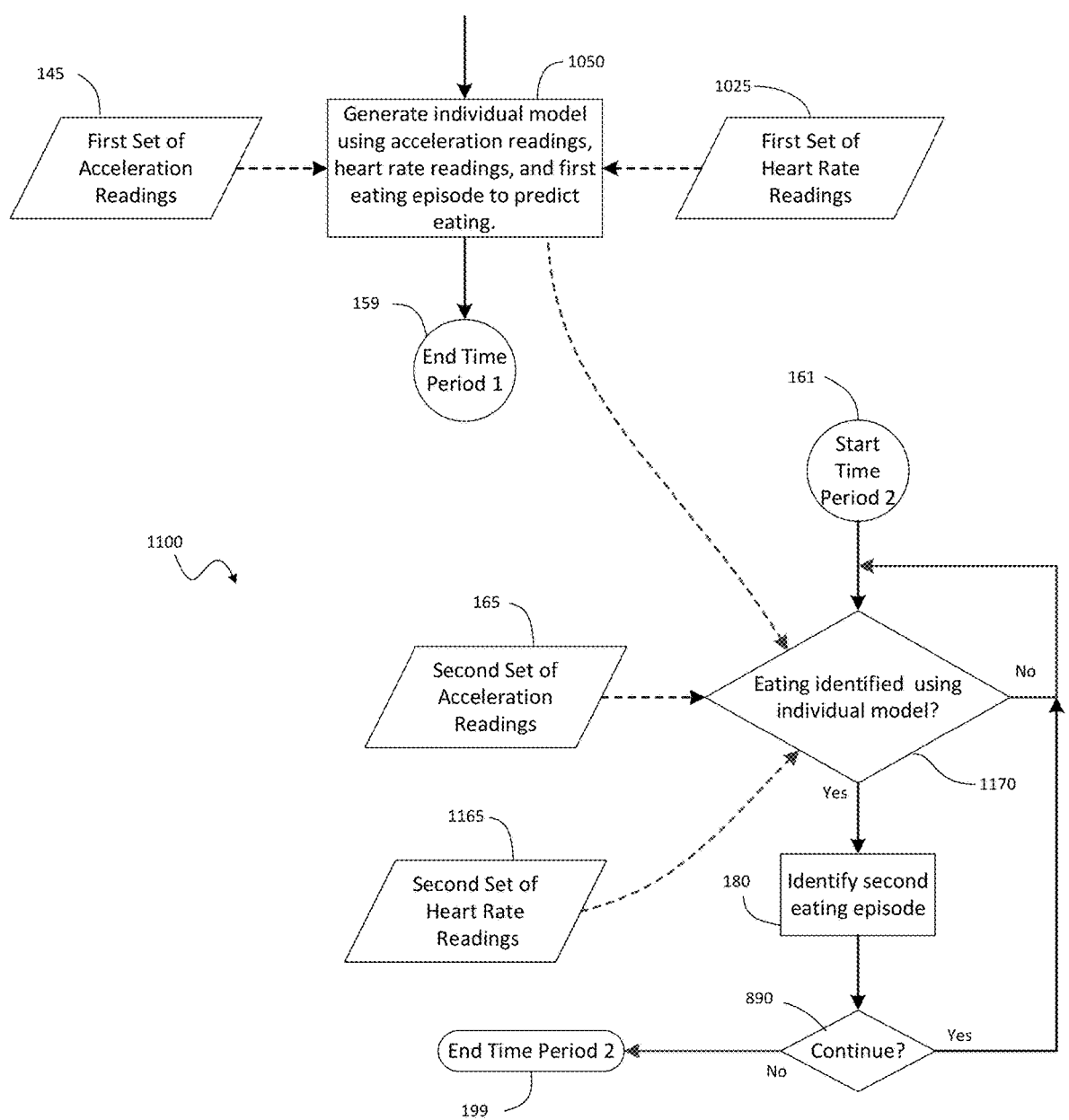
FIG. 11 presents a flowchart illustrating a method for detecting eating activity using acceleration readings and heart rate readings to identify a second eating episode, according to certain embodiments of the present disclosure.

FIG. 11 presents a flowchart illustrating a method (1100) for detecting eating activity using acceleration readings and heart rate readings to identify a second eating episode, according to certain embodiments of the present disclosure. Method 1100 begins after creation of an individual model predicting eating episodes using acceleration readings and heart rate readings as, for example, in FIG. 10. A second time period begins at 161. A processing unit (either the same used in the first time period or a second processing unit) applies an individual model to a second set of acceleration readings (165) and a second set of heart rate readings (1165), both sets of readings generated during the second time period, to determine if there is eating activity (1170). If the individual model indicates no activity, processing repeats step 1170 to monitor subsequent acceleration readings and PPG readings for eating activity. If eating activity is detected, the processing unit identifies a second eating episode (180). Processing then determines whether to continue monitoring for additional eating episodes (890). If additional monitoring is indicated, processing returns to step 1170. If no further monitoring is indicated, the method (1100) ends (199).

Detecting eating may be useful as an end in itself but may also be used as a means to accomplish other ends. For example, automated eating detection may be used as part of a program to influence eating behaviors that could be used to achieve ends such as weight loss or control of glucose levels. For example, if eating is detected a message may be sent to a user interface indicating that the recipient of the message, or an individual the recipient is coaching, eat or avoid particular types of food or limit the quantity of food eaten. In another embodiment, if acceleration readings indicate a threshold quantity of physical activity, but do not indicate eating for a threshold amount of time, the processing unit may send a message to a user interface indicating that it is time for the recipient or coached individual to eat in order to avoid hypoglycemia.

Figure 12:
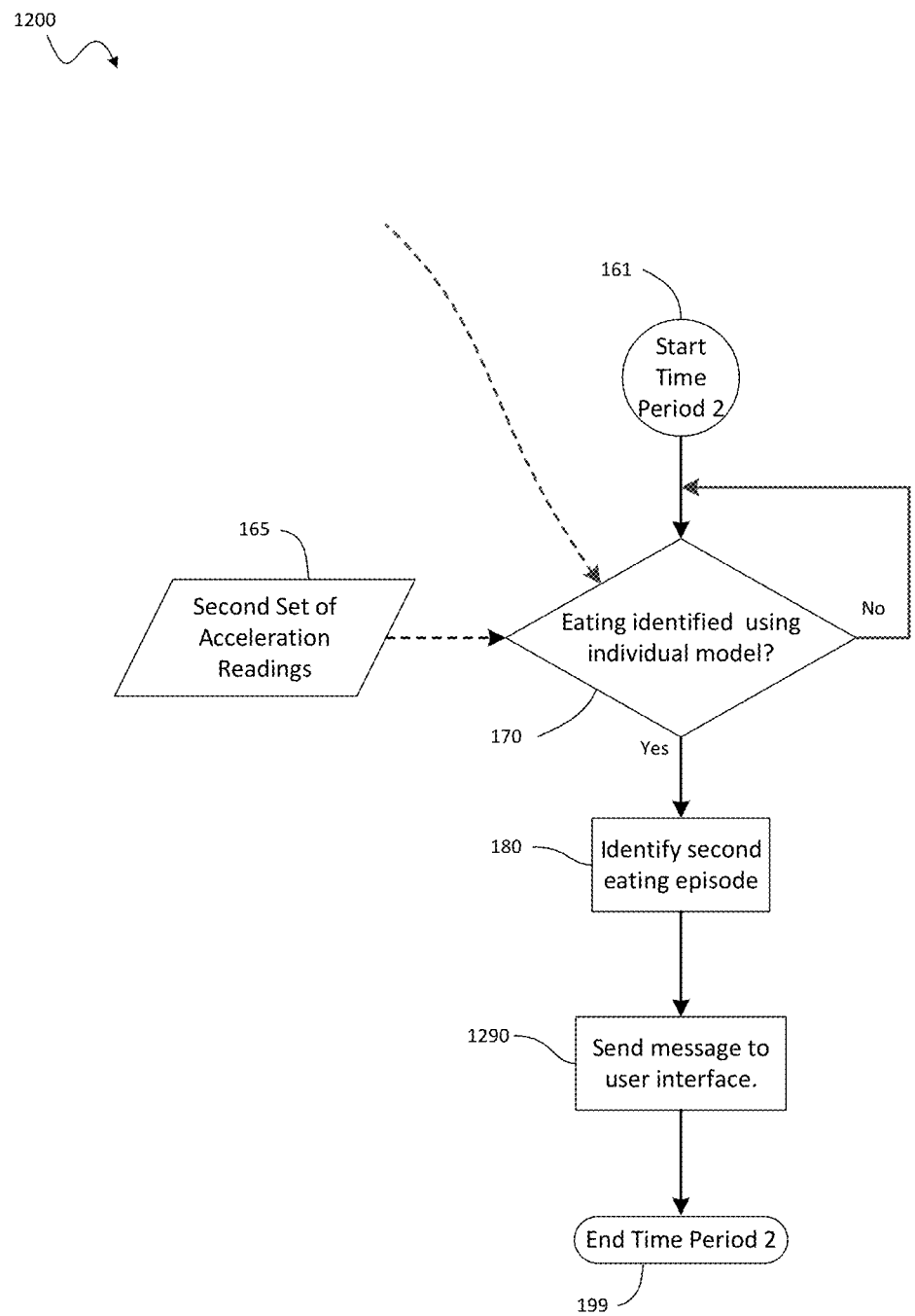
FIG. 12 presents a flowchart illustrating a method for detecting eating activity in which a message is sent to a user interface if a second eating episode is identified, according to certain embodiments of the present disclosure.

FIG. 12 presents a flowchart illustrating a method (1200) for detecting eating activity in which a message is sent to a user interface if a second eating episode is identified, according to certain embodiments of the present disclosure. Method 1200 begins after creation of an individual model predicting eating episodes using acceleration readings and heart rate readings as, for example, in FIG. 1. A second time period begins at 161. A processing unit (either the same used in the first time period or a second processing unit) applies the individual model to a second set of acceleration readings (165) generated during the second time period to determine whether eating activity is occurring (170). If the individual model indicates no activity, processing repeats step 170 to monitor acceleration readings for eating activity. If eating activity is detected, the processing unit identifies a second eating episode (180) and the processing unit sends a message to a user interface recommending a behavior that influences glucose levels (1290). The method (1200) ends at 199.

Machine learning encompasses a great variety of techniques. For any particular prediction task, some machine learning techniques may be more effective than others. In addition, there are multiple approaches to identifying eating activity from acceleration readings. Some approaches are binary, seeking to distinguish only between eating activity and any activity that is not eating. In particular, these approaches may seek to distinguish hand-to-mouth gestures from non-hand-to-mouth activity. Other approaches identify eating activity in addition to a number of other activity types. For example, a machine learning model may identify activity states for physical exercise, tooth brushing, and piano playing in addition to eating.

Applicant has experimented with a number of different machine learning techniques and approaches to classifying acceleration data and found some to work particularly well. Hidden Markov models (HMMs) proved particularly effective at distinguishing hand-to-mouth gestures from non-hand-to-mouth activity. For approaches distinguishing multiple activity states, long short term memory (LSTM) functions used with a time-distributed layer-recursive neural network classifier (TDLRNNC) yielded results superior to other methods. Use of a two-stacked LSTM proved particularly effective. Contrary to what intuition might suggest, approaches identifying multiple activity states in addition to eating proved more accurate than binary eating/non-eating models outside of the laboratory setting. The Appendix attached hereto displays code used to generate individual models using HMM, LSTM, and neural networks.

Figure 13:
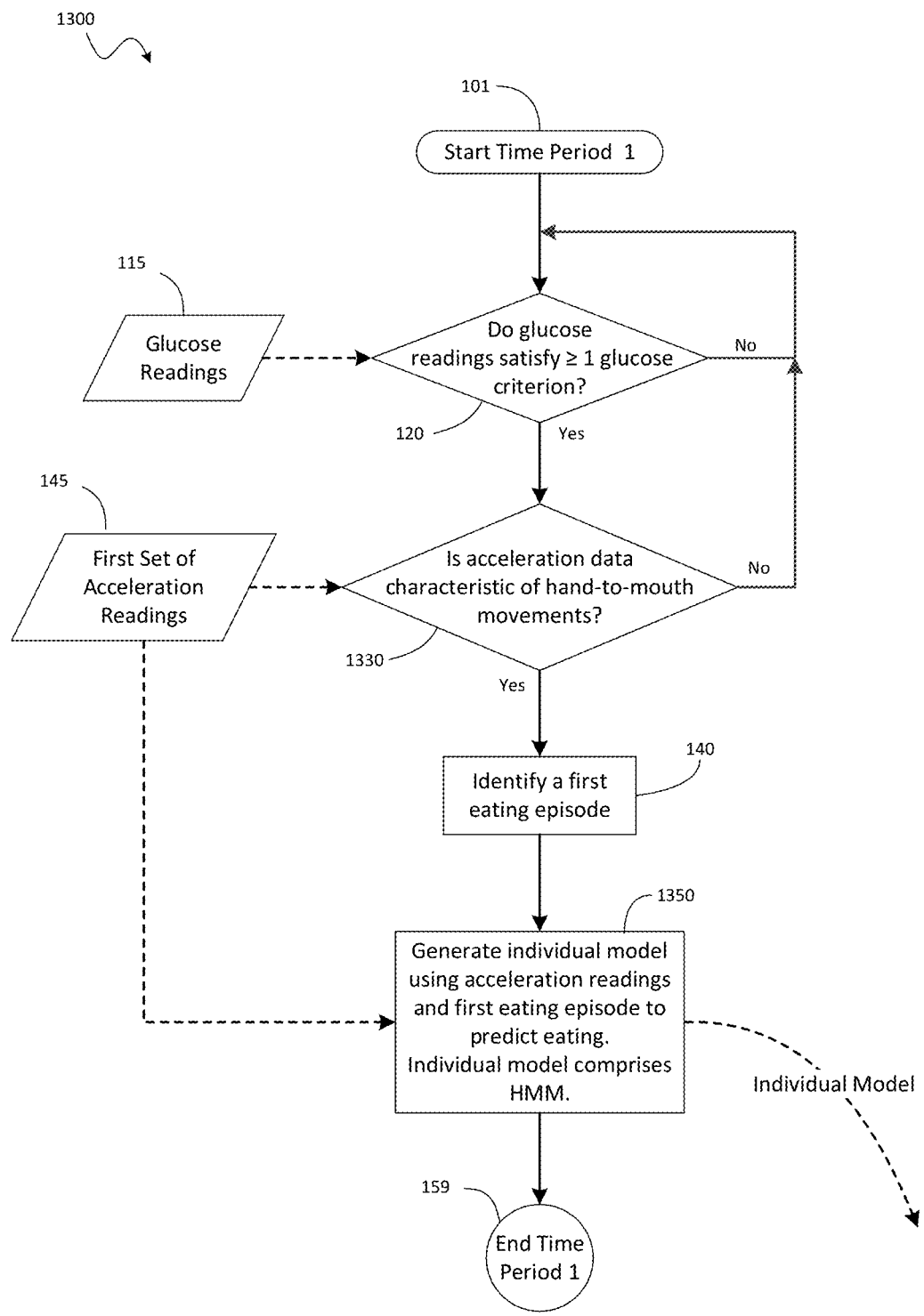
FIG. 13 presents a flowchart illustrating a method for detecting eating activity using a long-short term memory function and time-distributed, layer recursive, neural network classifier, according to certain embodiments of the present disclosure.

FIG. 13 presents a flowchart illustrating a method (1300) for detecting eating activity using a hidden Markov model (HMM) to identify hand-to-mouth movements, according to certain embodiments of the present disclosure. After the start of a first time period (101), a processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit determines whether a first set of acceleration readings (145) generated during the first time period is characteristic of hand-to-mouth movements (1330). If not, processing returns to step 120 to determine whether subsequent glucose readings satisfy the one or more glucose criteria. If the acceleration readings (145) are characteristic of hand-to-mouth movements, the processing unit identifies a first eating episode (140). Using the first set of acceleration readings (145), the processing unit generates an individual model comprising a hidden Markov model (HMM) predicting eating episodes using at least the first eating episode as training data (1350). The individual model identifies hand-to-mouth gestures in acceleration readings using the HMM. Collection of training data ceases at the end of the first time period (159). The individual model may then be used to identify eating episodes using acceleration readings during a second time period, as described in FIG. 1 and elsewhere herein.

Figure 14:
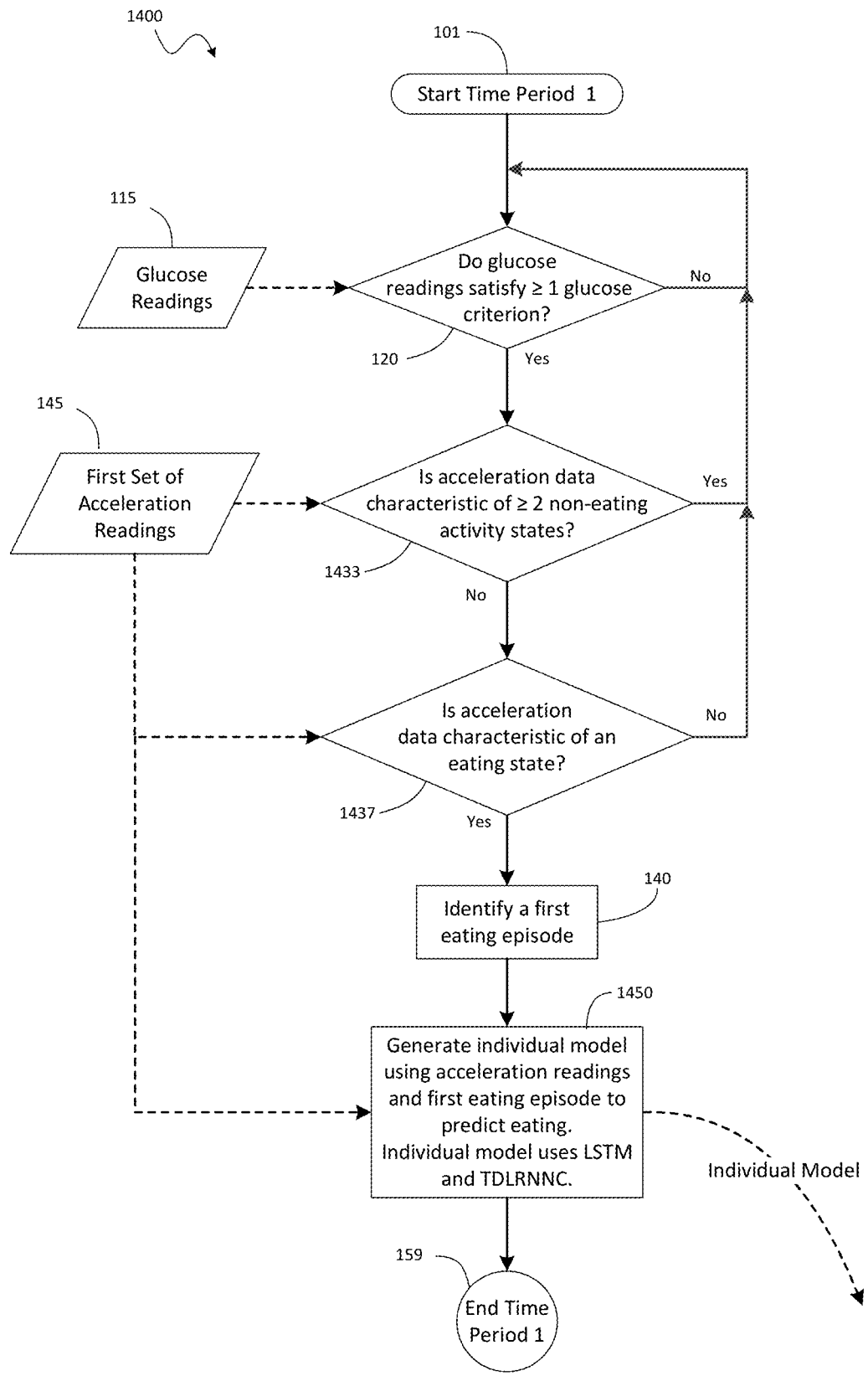
FIG. 14 presents a flowchart illustrating a method for detecting eating activity using a hidden Markov model to identify hand-to-mouth movements, according to certain embodiments of the present disclosure.

FIG. 14 presents a flowchart illustrating a method (1400) for detecting eating activity among multiple activity types using a long-short term memory (LSTM) function and a time-distributed, layer recursive, neural network classifier (TDLRNNC), according to certain embodiments of the present disclosure. After the start of a first time period (101), a processing unit determines whether glucose readings (115) generated during the first time period satisfy one or more glucose criteria (120). If not, processing repeats step 120 to determine whether subsequent glucose readings satisfy the one or more glucose criteria. If the glucose readings satisfy the one or more glucose criteria, the processing unit determines whether a first set of acceleration readings (145) generated during the first time period is characteristic of two or more non-eating activity states (1433). If so, processing returns to step 120 to determine whether subsequent glucose readings satisfy the one or more glucose criteria. If the first set of acceleration readings (145) are not characteristic of two or more non-eating states, the processing unit determines whether the first set of acceleration readings (145) are characteristic of an eating state (1437). If not, processing returns to step 120 to determine whether subsequent glucose readings satisfy the one or more glucose criteria. If the first set of acceleration readings (145) are characteristic of an eating state, the processing unit identifies a first eating episode (140). Using the first set of acceleration readings (145), the processing unit generates an individual model comprising a long-short term memory (LSTM) function and a time-distributed, layer recursive, neural network classifier (TDLRNNC) (1450). The individual model predicts eating episodes using at least the first eating episode as training data. The individual model identifies movements characteristic of eating using the LSTM function and TDLRNNC. Collection of training data ceases at the end of the first time period (159). The individual model may then be used to identify eating episodes using acceleration readings during a second time period, as described in FIG. 1 and elsewhere herein.

Systems:

System embodiments may include a glucose sensor and an accelerometer communicatively coupled to a processing unit. The processing unit may, optionally, be communicatively coupled to a user interface. System components may be housed in a single device or be distributed among multiple devices. Communicative coupling does not necessarily require a physical connection and indicates only that one system component may send or receive information to or from another. If one component is communicatively coupled to another, it may be referred to as being in communication with the other component. One component may be communicatively coupled to another if, for example, it sends or receives electromagnetic transmissions to or from the other component.

A glucose sensor may refer to any device or component that measures glucose levels. The output of the monitor may be analog, digital, or of other format and may or may not require other devices or components to convert the output of the glucose sensor into a glucose level. Glucose sensors may include, for example, those in direct contact with blood or other bodily fluids or tissues or those measuring glucose without direct contact including transmission and reflection spectroscopy. Continuous glucose monitoring (CGM) includes a variety of devices and techniques that measure glucose more frequently than was practical with earlier methods. In the context of CGM, continuous does not require that readings are either instantaneous or absolutely continuous. For example, CGM devices may provide measurements every five to ten minutes.

Figure 15:
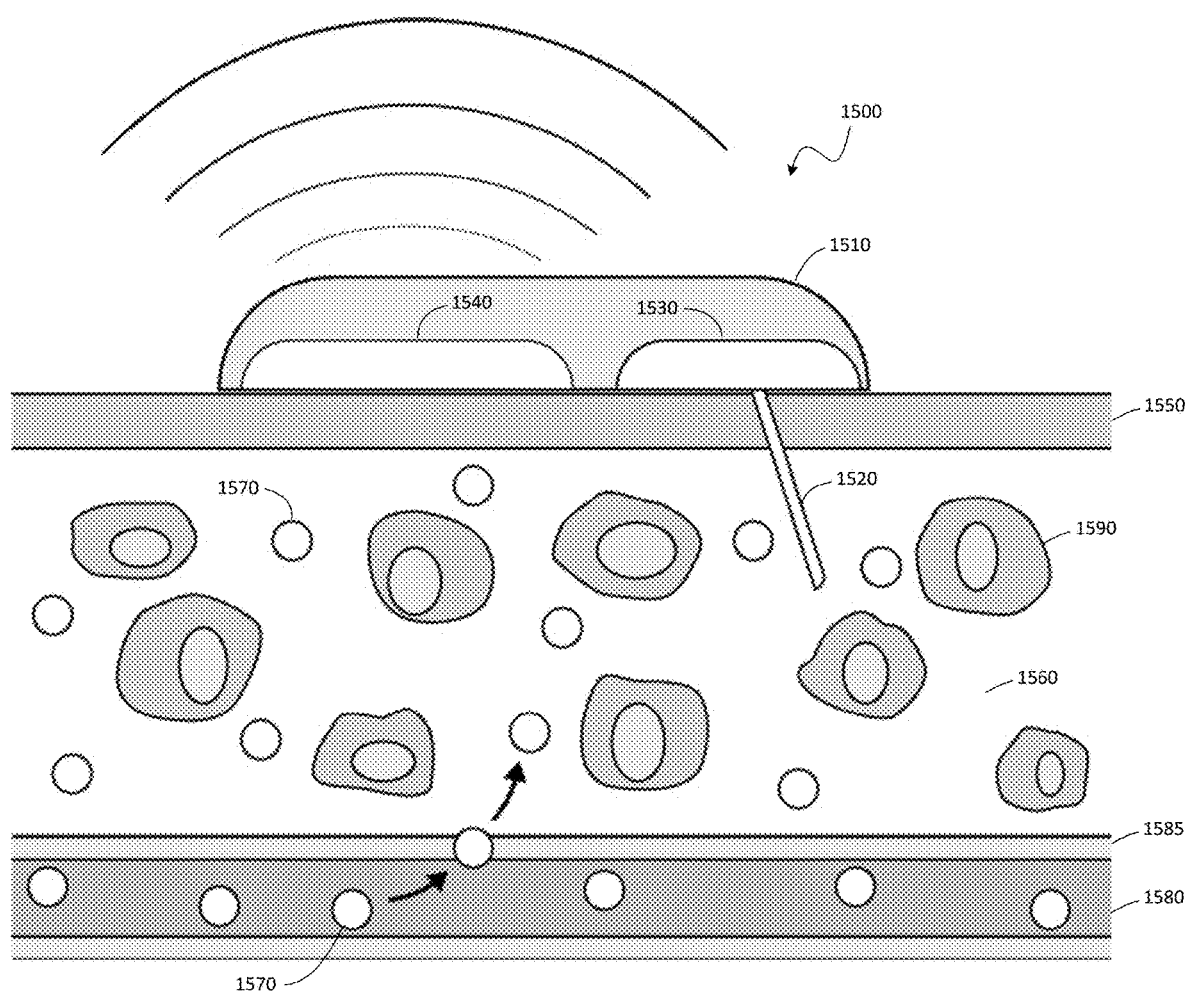
FIG. 15 presents a diagram depicting an embodiment of a continuous glucose monitor (CGM), according to certain embodiments of the present disclosure.

FIG. 15 presents a diagram depicting an embodiment of a continuous glucose monitor (CGM). The CGM (1500) comprises a housing (1510), a sensor wire (1520), detection electronics (1530), and a transmitter (1540). The sensor wire (1520) traverses the skin (1550) so that it comes in contact with interstitial fluid (1560). Glucose molecules (1570) in the blood stream (1580) pass through the wall of a blood vessel (1585) and into the interstitial fluid (1560). Once in the interstitial fluid (1560), glucose molecules (1570) may be absorbed by cells (1590) in the interstitial fluid or come in contact with the sensor wire (1520). The detection electronics (1530) detect the concentration of glucose (1570) in contact with the sensor wire (1520) and relay glucose to the transmitter (1540). The transmitter (1540) then transmits the glucose readings over radio frequencies.

An accelerometer may refer to any device that measures either linear or angular acceleration. However, accelerometers measuring angular acceleration may also be referred to as gyroscopes, gyrometers, or simply gyros. An accelerometer may also refer to a device that measures acceleration in more than one direction and/or that measures both linear and angular acceleration. Devices referred to as nine-axis accelerometers measure both linear and angular acceleration along or around (respectively) three orthogonal axes as well as orientation of the accelerometer relative to magnetic fields such as that of the Earth. The axes of accelerometers with multiple axes may be orthogonal or approximately orthogonal. Acceleration readings may be used to estimate derived quantities of physical activity such as step count, calories burned, or distance traveled.

Figure 16:
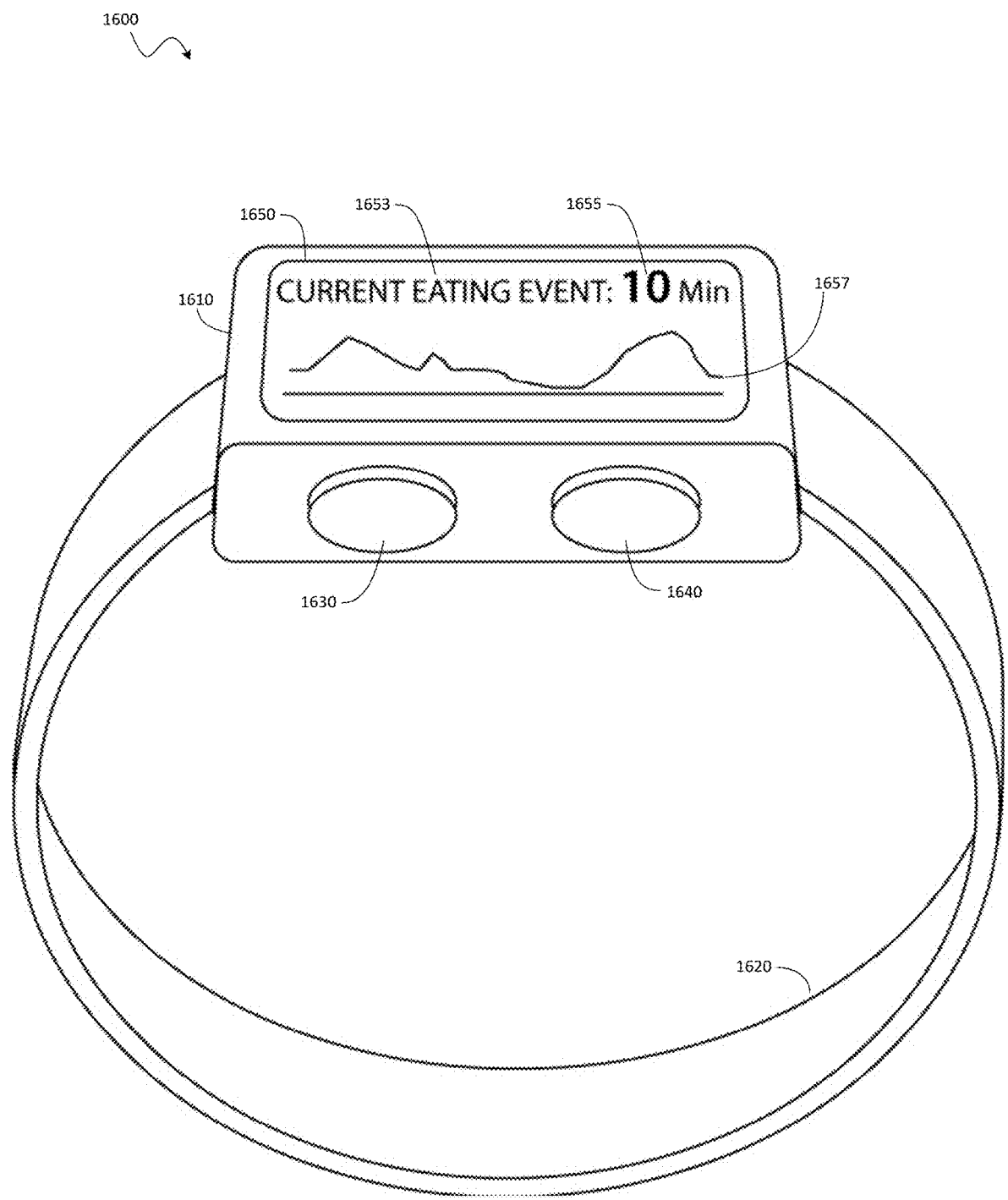
FIG. 16 presents a diagram depicting an embodiment of a wrist-worn device for detecting eating episodes comprising an accelerometer, according to certain embodiments of the present disclosure.

FIG. 16 presents a diagram depicting an embodiment of a wearable device (1600) for detecting eating episodes. The device (1600) comprises a device housing (1610) and a strap (1620). An accelerometer (not visible) may be located in the device housing (1610). The strap (1620) may be used to secure the device housing (1610) to an individual, for example by placing the strap (1620) around the wrist, hand, or forearm. Two buttons (1630, 1640) protrude from the side of the device housing (1610) and may be used to, for example, turn the device on and off, transition among different functions of the device, or to signal the beginning or end of an eating episode. The device (1600) comprises a display screen (1650) visible at a top surface of the device (1600). The display screen (1650) comprises a description of the current state (1653) as determined using acceleration readings from the accelerometer. In this particular illustration, the description of the state (1653) is identified as being an eating event. Other potential states may include a non-eating state, or other activity states such as physical exercise, sleep, or brushing teeth. The display screen (1650) also comprises a duration (1655) of the current state. The display screen (1650) further comprises a graph (1657) of activity level which may be indicative of an activity state of the individual wearing the device (1600). A device such as device 1600 may comprise a processing unit configured to apply an individual model of eating motions to motions detected by the accelerometer housed within. The device (1600) may optionally comprise a transmitter (not visible) to communicate acceleration readings to an external processing unit for purposes of generating an individual model of eating. The device (1600) may optionally comprise a PPG sensor or a heart rate sensor (not visible).

The glucose monitor and accelerometer may be communicatively coupled to a processing unit configured, though design or programming, to process outputs from the respective sensor types. Processing units may comprise one or more processors and any memory or other data storage necessary to process and store data. A processing unit may store instructions executed by the one or more processors. If a processing unit comprises more than one processor, the multiple processors need not be located in close physical proximity to one another. Therefore, steps of methods performed on a single processing unit may be performed by multiple processors at multiple locations and multiple times.

Figure 17:
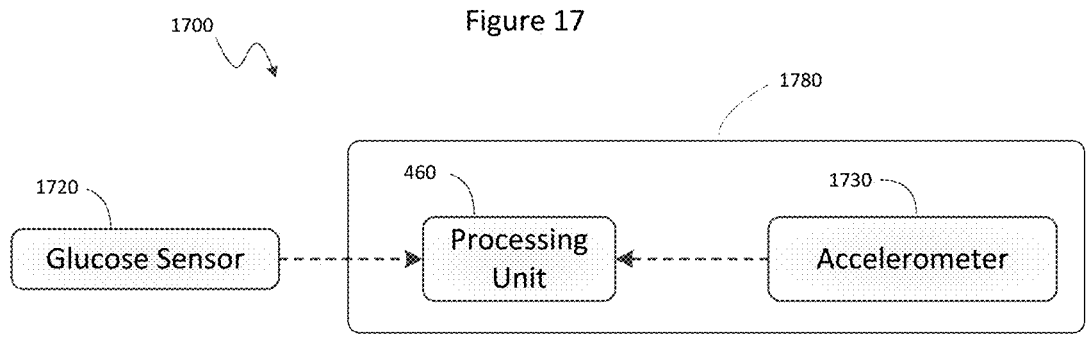
FIG. 17 presents a schematic diagram depicting an embodiment of a system for detecting eating episodes comprising a glucose sensor, a processing unit, and an accelerometer, according to certain embodiments of the present disclosure.

FIG. 17 presents a schematic diagram depicting an embodiment of a system (1700) for detecting eating episodes. The system (1700) comprises a glucose sensor (1720) and an accelerometer (1730), each communicatively coupled to a processing unit (460), according to the present disclosure. The dashed lines connecting the components indicate that they are communicatively coupled; information may be transferred from one to another, but does not necessarily require a physical connection. The processing unit (460) and accelerometer (1730) may be housed in a single device (1780) such as, for example, that illustrated in FIG. 16. The glucose sensor may be part of a CGM device such as, for example, that illustrated in FIG. 15. The processing unit (460) receives a set of glucose readings generated by the glucose sensor (1720) during a first time period and a first set of acceleration readings generated by the accelerometer (1730) during the first time period. The processing unit (460) identifies a first eating episode if the set of glucose readings satisfies one or more glucose criteria and generates an individual model using the first set of acceleration readings and the first eating episode. The individual model uses acceleration readings corresponding to motion of the hand of the individual to identify eating episodes and does not use glucose readings. The processing unit (460) receives a second set of acceleration readings generated by the accelerometer (1730) during a second time period and identifies a second eating episode using the individual model and the second set of acceleration readings.

As discussed herein, methods may be performed by one or more processing units to detect eating episodes. Similarly, methods may use a single accelerometer during both the training and subsequent detection periods, or use multiple accelerometers during these periods.

Figure 18:
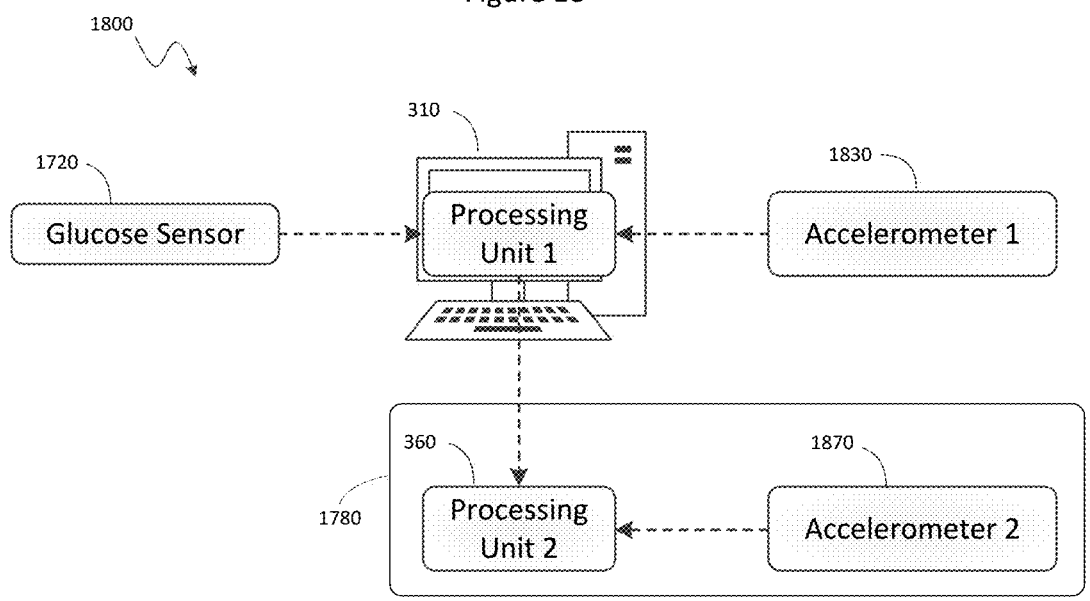
FIG. 18 presents a schematic diagram depicting an embodiment of a system for detecting eating episodes comprising a glucose sensor, two processing units, and two accelerometers, according to certain embodiments of the present disclosure.

FIG. 18 presents a schematic diagram depicting an embodiment of a system (1800) for detecting eating episodes comprising two processing units (310, 360), a glucose sensor (1720), and two accelerometers (1830, 1870), according to the present disclosure. The glucose sensor (1720) and first accelerometer (1830) are each communicatively coupled to the first processing unit (310). The dashed lines connecting the components indicate that they are communicatively coupled; information may be transferred from one to another, but does not necessarily require a physical connection. The first processing unit may be housed, for example, in a personal computer. The second accelerometer (1870) is communicatively coupled to the second processing unit (360). The second processing unit (360) and second accelerometer (1870) may be housed in a single device (1780) such as, for example, that illustrated in FIG. 16. The first processing unit (310) is communicatively coupled to the second processing unit (360) at least for purposes of communicating a personal model of eating motion. The first processing unit (310) receives a set of glucose readings generated by the glucose sensor (1720) during a first time period and a first set of acceleration readings generated by the first accelerometer (1830) during the first time period. The first processing unit (310) identifies a first eating episode if the set of glucose readings satisfies one or more glucose criteria and generates an individual model using the first set of acceleration readings and the first eating episode. The individual model uses acceleration readings corresponding to motion of the hand of the individual to identify eating episodes and does not use glucose readings. The first processing unit (310) communicates the individual model to the second processing unit (360). The second processing unit (360) receives a second set of acceleration readings generated by the second accelerometer (1870) during a second time period and identifies a second eating episode using the individual model and the second set of acceleration readings.

Figure 19:
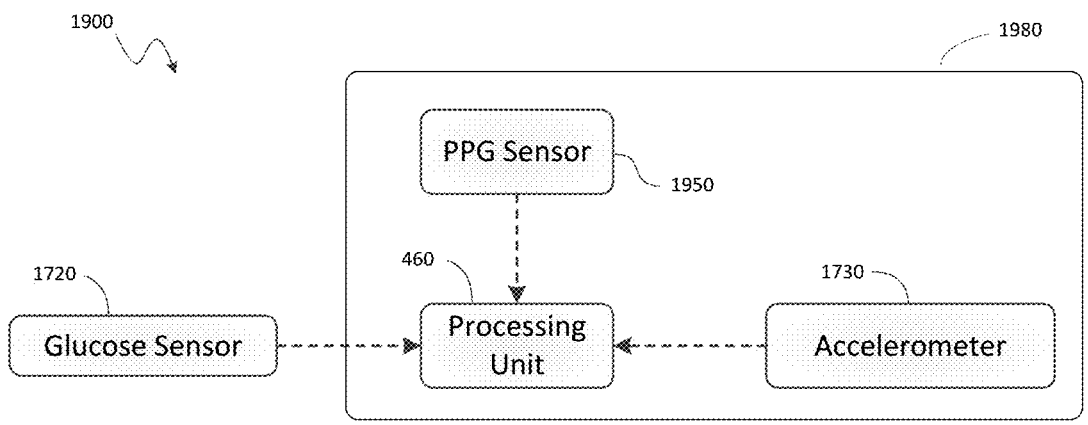
FIG. 19 presents a schematic diagram depicting an embodiment of a system for detecting eating episodes comprising a PPG sensor, a glucose sensor, a processing unit, and an accelerometer, according to certain embodiments of the present disclosure.

Some methods use PPG readings to add predictive value to the glucose readings and/or acceleration readings. FIG. 19 presents a schematic diagram depicting an embodiment of a system (1900) for detecting eating episodes comprising a PPG sensor (1950), a glucose sensor (1720), and an accelerometer (1730) each communicatively coupled to a processing unit (460), according to certain embodiments of the present disclosure. The dashed lines connecting the components indicate that they are communicatively coupled; information may be transferred from one to another, but does not necessarily require a physical connection. The processing unit (460), PPG sensor (1950), and accelerometer (1730) may be housed in a single device (1980) such as, for example, that illustrated in FIG. 16. The processing unit (460) receives: a set of glucose readings generated by the glucose sensor (1720) during a first time period; a first set of acceleration readings generated by the accelerometer (1730) during the first time period; and a first set of PPG readings generated by the PPG sensor (1950) during the first time period. The processing unit (460) identifies a first eating episode if the set of glucose readings satisfies one or more glucose criteria and generates an individual model using the first set of acceleration readings, the first set of PPG readings, and the first eating episode. The individual model uses acceleration readings corresponding to motion of the hand of the individual and PPG readings of the individual to identify eating episodes and does not use glucose readings. The processing unit (460) receives a second set of acceleration readings generated by the accelerometer (1730) during a second time period and a second set of PPG readings generated by the PPG sensor (1950) during the second time period. The processing unit (460) identifies a second eating episode using the individual model, the second set of PPG readings, and the second set of acceleration readings.

Figure 20:
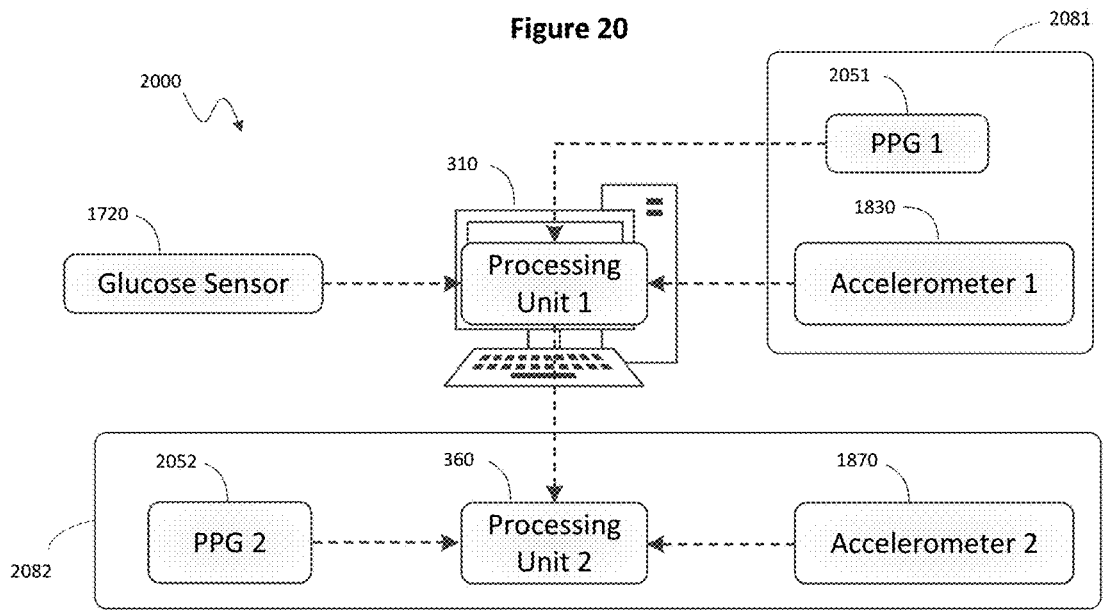
FIG. 20 presents a schematic diagram depicting an embodiment of a system for detecting eating episodes comprising a glucose sensor, two processing units, two accelerometers, and two PPG sensors, according to certain embodiments of the present disclosure.

As discussed with processing units and accelerometers, methods involving PPG readings may be performed using a single PPG sensor during both the training and subsequent detection periods, or use multiple PPG sensors during these periods. FIG. 20 presents a schematic diagram depicting an embodiment of a system for detecting eating episodes comprising a glucose sensor (1720), two processing units (310, 360), two accelerometers (1830, 1870), and two PPG sensors (2051, 2052), according to certain embodiments of the present disclosure. The glucose sensor (1720), first accelerometer (1830), and first PPG sensor (2051) are each communicatively coupled to the first processing unit (310). The dashed lines connecting the components indicate that they are communicatively coupled; information may be transferred from one to another, but does not necessarily require a physical connection. The first PPG sensor (2051) and first accelerometer (1870) may be housed in a single device (2081) such as, for example, that illustrated in FIG. 16. The second accelerometer (1870) and second PPG sensor (2052) are communicatively coupled to the second processing unit (360). The second processing unit (360), second PPG sensor, and second accelerometer (1870) may be housed in a single device (2082) such as, for example, that illustrated in FIG. 16. The first processing unit (310) is communicatively coupled to the second processing unit (360) at least for purposes of communicating a personal model of eating motion. The first processing unit (310) receives a set of glucose readings generated by the glucose sensor (1720) during a first time period, a first set of acceleration readings generated by the first accelerometer (1830) during the first time period, and a first set of PPG readings generated by the first PPG sensor (2051) during the first time period. The first processing unit (310) identifies a first eating episode if the set of glucose readings satisfies one or more glucose criteria and generates an individual model using the first set of acceleration readings, the first set of PPG readings, and the first eating episode. The individual model uses acceleration readings corresponding to motion of the hand of the individual and PPG readings from the individual to identify eating episodes and does not use glucose readings. The first processing unit (310) communicates the individual model to the second processing unit (360). The second processing unit (360) receives a second set of acceleration readings generated by the second accelerometer (1870) during a second time period and a second set of PPG readings generated by the second PPG sensor (2052) during the second time period. The second processing unit (360) identifies a second eating episode using the individual model, the second set of acceleration readings, and the second set of PPG readings.

Figure 21:
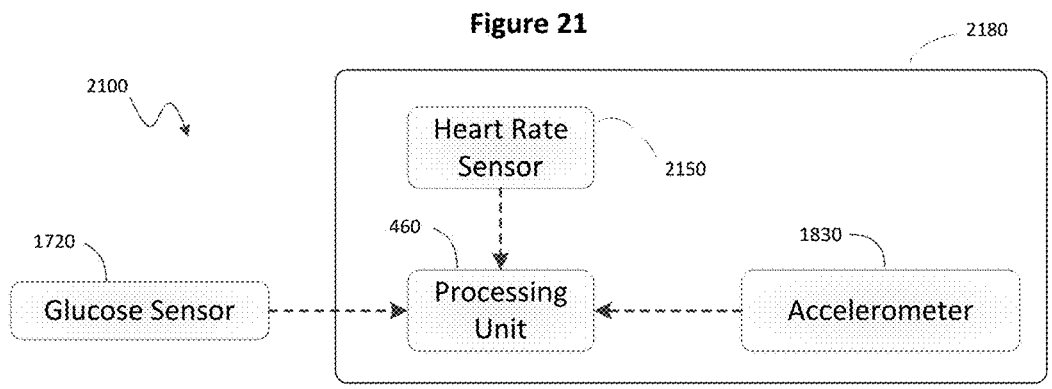
FIG. 21 presents a schematic diagram depicting an embodiment of a system for detecting eating episodes comprising a heart rate sensor, a glucose sensor, a processing unit, and an accelerometer, according to certain embodiments of the present disclosure.

Some methods use heart rate readings to add predictive value to the glucose readings and/or acceleration readings. FIG. 21 presents a schematic diagram depicting an embodiment of a system (2100) for detecting eating episodes comprising a heart rate sensor (2150), a glucose sensor (1720), and an accelerometer (1730) each communicatively coupled to a processing unit (460), according to certain embodiments of the present disclosure. The dashed lines connecting the components indicate that they are communicatively coupled; information may be transferred from one to another, but does not necessarily require a physical connection. The processing unit (460), heart rate sensor (2150), and accelerometer (1730) may be housed in a single device (2180) such as, for example, that illustrated in FIG. 16. The processing unit (460) receives: a set of glucose readings generated by the glucose sensor (1720) during a first time period; a first set of acceleration readings generated by the accelerometer (1730) during the first time period;

and a first set of heart rate readings generated by the heart rate sensor (2150) during the first time period. The processing unit (460) identifies a first eating episode if the set of glucose readings satisfies one or more glucose criteria and generates an individual model using the first set of acceleration readings, the first set of heart rate readings, and the first eating episode. The individual model uses acceleration readings corresponding to motion of the hand of the individual and heart rate readings of the individual to identify eating episodes and does not use glucose readings. The processing unit (460) receives a second set of acceleration readings generated by the accelerometer (1730) during a second time period and a second set of heart rate readings generated by the heart rate sensor (2150) during the second time period. The processing unit (460) identifies a second eating episode using the individual model, the second set of heart rate readings, and the second set of acceleration readings.

Figure 22:
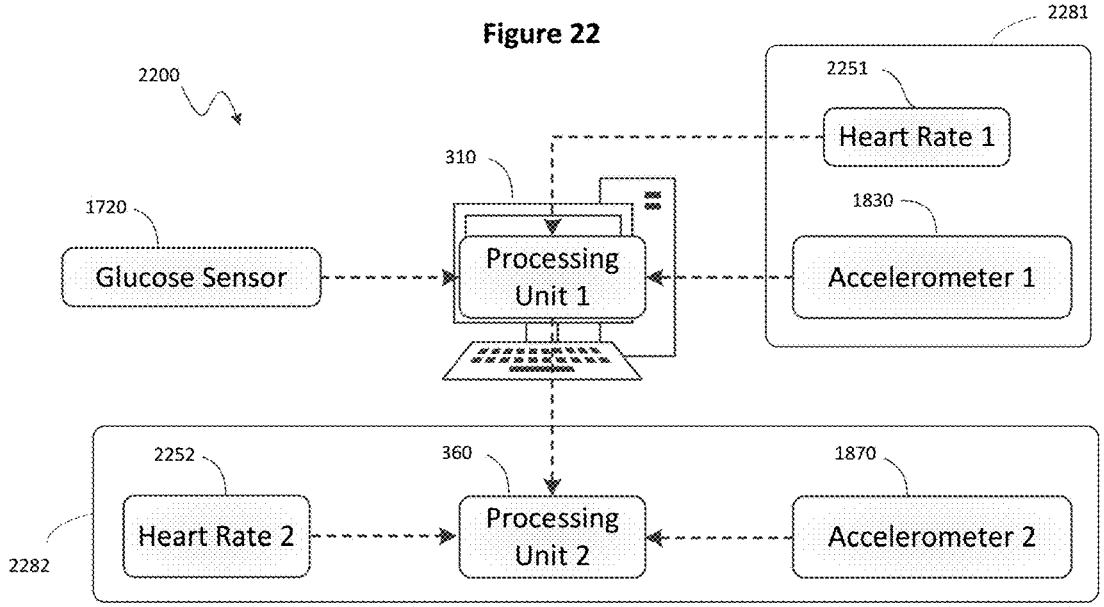
FIG. 22 presents a schematic diagram depicting an embodiment of a system for detecting eating episodes comprising a glucose sensor, two processing units, two accelerometers, and two heart rate sensors, according to certain embodiments of the present disclosure.

As discussed with processing units and accelerometers, methods involving heart rate readings may be performed using a single heart rate sensor during both the training and subsequent detection periods, or use multiple heart rate sensors during these periods. FIG. 22 presents a schematic diagram depicting an embodiment of a system for detecting eating episodes comprising a glucose sensor (1720), two processing units (310, 360), two accelerometers (1830, 1870), and two heart rate sensors (2251, 2252), according to certain embodiments of the present disclosure. The glucose sensor (1720), first accelerometer (1830), and first heart rate sensor (2251) are each communicatively coupled to the first processing unit (310). The dashed lines connecting the components indicate that they are communicatively coupled; information may be transferred from one to another, but does not necessarily require a physical connection. The first heart rate sensor (2251) and first accelerometer (1870) may be housed in a single device (2281) such as, for example, that illustrated in FIG. 16. The second accelerometer (1870) and second heart rate sensor (2252) are communicatively coupled to the second processing unit (360). The second processing unit (360), second heart rate sensor, and second accelerometer (1870) may be housed in a single device (2282) such as, for example, that illustrated in FIG. 16. The first processing unit (310) is communicatively coupled to the second processing unit (360) at least for purposes of communicating a personal model of eating motion. The first processing unit (310) receives a set of glucose readings generated by the glucose sensor (1720) during a first time period, a first set of acceleration readings generated by the first accelerometer (1830) during the first time period, and a first set of heart rate readings generated by the first heart rate sensor (2251) during the first time period. The first processing unit (310) identifies a first eating episode if the set of glucose readings satisfies one or more glucose criteria and generates an individual model using the first set of acceleration readings, the first set of heart rate readings, and the first eating episode. The individual model uses acceleration readings corresponding to motion of the hand of the individual and heart rate readings from the individual to identify eating episodes and does not use glucose readings. The first processing unit (310) communicates the individual model to the second processing unit (360). The second processing unit (360) receives a second set of acceleration readings generated by the second accelerometer (1870) during a second time period and a second set of heart rate readings generated by the second heart rate sensor (2252) during the second time period. The second processing unit (360) identifies a second eating episode using the individual model, the second set of acceleration readings, and the second set of heart rate readings.

The above description is neither exclusive nor exhaustive and does not necessarily describe all possible embodiments (also called "examples") nor is intended to limit the scope of the claims. Embodiments may include elements in addition to those described and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless otherwise indicated. Terms such as "first," "second," "third" and so forth are used as labels to distinguish elements and do not indicate sequential order unless otherwise indicated. In addition to the embodiments described above, embodiments include any that would fall within the scope of the claims, below.

What is claimed is:

1. A method for using machine learning to detect eating activity of an individual, the method comprising:

receiving, by an apparatus comprising one or more processors, a set of glucose readings, wherein (a) the set of glucose readings corresponds to glucose levels of the individual during a first time period, (b) the set of glucose readings is captured during the first time period by a continuous glucose monitoring (CGM) device coupled to the individual, (c) the CGM device comprises a glucose sensor that collects CGM glucose readings, and (d) the set of glucose readings is wirelessly transmitted to the apparatus by the CGM device;

determining, by the apparatus comprising the one or more processors, that the set of glucose readings satisfies one or more glucose criteria indicative of a first eating episode;

responsive to determining that the set of glucose readings satisfies the one or more glucose criteria indicative of the first eating episode, determining, by the apparatus comprising the one or more processors, whether a set of photo-plethysmograph (PPG) readings satisfies one or more PPG criteria indicative of the first eating episode, wherein (a) the set of PPG readings corresponds to blood flow during the first time period, (b) the set of PPG readings is captured during the first time period by a wearable device worn by the individual, (c) the wearable device comprises both a PPG sensor that collects PPG readings and an accelerometer that collects accelerometer readings, and (d) the set of PPG readings is wirelessly transmitted to the apparatus by the wearable device;

responsive to determining that the set of PPG readings satisfies one or more PPG criteria indicative of the first eating episode, identifying, by the apparatus comprising the one or more processors, a first set of acceleration readings as training data for training a machine learning model configured to generate predictions of eating episodes, wherein (a) the first set of acceleration readings corresponds to motion of a hand of the individual, and (b) the first set of acceleration readings is captured during the first time period by the accelerometer of the wearable device;

programmatically training, by the apparatus comprising the one or more processors, the machine learning model, wherein the trained machine learning model (a) generates predictions of eating episodes based at least in part on acceleration readings, and (b) is stored in one or more memory storage areas accessible by the apparatus;

receiving, by the apparatus comprising the one or more processors, a second set of acceleration readings, wherein (a) the second set of acceleration readings corresponds to motion of the hand of the individual, and (b) the second set of acceleration readings is captured during a second time period by the accelerometer of the wearable device;

generating, by the apparatus comprising the one or more processors and using the trained machine learning model and the second set of acceleration readings, a prediction that the second set of acceleration readings indicates a second eating episode; and providing, by the apparatus comprising the one or more processors, an indication of the prediction that the second set of acceleration readings indicates a second eating episode to the wearable device, wherein the wearable device causes display of at least a portion of the indication.

2. The method of claim 1, wherein the one or more glucose criteria comprise one or more of (a) at least one of the set glucose readings exceeding a threshold glucose level, (b) a rate of glucose change exceeding a threshold rate of glucose change, or (c) a derivative of the rate of glucose change exceeding a threshold for the derivative of the rate of glucose change.

3. The method of claim 1, wherein (a) the set glucose readings exhibits one or more characteristics within a threshold amount of time before a second condition, (b) the set glucose readings exhibits one or more characteristics within a threshold amount of time after a second condition, (c) the set glucose readings exhibits one or more characteristics within a particular time range, or (d) the set glucose readings exhibits one or more characteristics for a particular duration.

4. The method of claim 1 further comprising applying a population-based model of eating movement to the first set of acceleration readings, the population-based model identifying a potential eating episode, wherein the one or more glucose criteria comprise a criterion that the set glucose readings exhibit one or more characteristics within a threshold amount of time of the potential eating episode.

5. The method of claim 1 further comprising:
receiving a set of heart rate readings corresponding to a heart beat of the individual, wherein the set of heart rate readings is captured during the first time period and
determining that the set of heart rate readings satisfies one or more heart rate criteria.

6. The method of claim 5, wherein (a) a heart rate sensor is coupled to the individual, and (b) the heart rate sensor captures the set of heart rate readings of the individual.

7. The method of claim 1 further comprising:
receiving a first set of heart rate readings corresponding to a heart beat of the individual, wherein (a) the first set of heart rate readings is captured during the first time period, and (b) the machine learning model is further generated using at least a portion of the first set of heart rate readings as training data; and
receiving a second set of heart rate readings corresponding to the heart beat of the individual, wherein (a) the second set of heart rate readings is captured by the heart rate sensor during the second time period, and (b) the prediction using the machine learning model is based at least in part on the second set of acceleration readings and the second set of heart rate readings.

8. The method of claim 7, wherein (a) a heart rate sensor is coupled to the individual, and (b) the heart rate sensor captures the first set of heart rate readings or the second set of heart rate readings.

9. The method of claim 1 further comprising providing a notification of the second eating event.

10. The method of claim 1, wherein the machine learning model is selected from the group consisting of an LSTM (long short term memory) model, a time distributed layer recursive neural network classifier model, and a hidden Markov model.

11. A system for using machine learning to detect eating activity of an individual, the system comprising one or more processors and one or more memory storage areas, the system configured to:

receive a set of glucose readings, wherein (a) the set of glucose readings corresponds to glucose levels of the individual during a first time period, (b) the set of glucose readings is captured during the first time period by a continuous glucose monitoring (CGM) device coupled to the individual, (c) the CGM device comprises a glucose sensor that collects CGM glucose readings, and (d) the set of glucose readings is wirelessly transmitted to the system by the CGM device;

determine that the set of glucose readings satisfies one or more glucose criteria indicative of a first eating episode;

responsive to determining that the set of glucose readings satisfies the one or more glucose criteria indicative of the first eating episode, determine whether a set of photo-plethysmograph (PPG) readings satisfies one or more PPG criteria indicative of the first eating episode, wherein (a) the set of PPG readings corresponds to blood flow during the first time period, (b) the set of PPG readings is captured during the first time period by a wearable device worn by the individual, (c) the wearable device comprises both a PPG sensor that collects PPG readings and an accelerometer that collects accelerometer readings, and (d) the set of PPG readings is wirelessly transmitted to the system by the wearable device;

responsive to determining that the set of PPG readings satisfies one or more PPG criteria indicative of the first eating episode, identify a first set of acceleration readings as training Response dated data for training a machine learning model configured to generate predictions of eating episodes, wherein (a) the first set of acceleration readings corresponds to motion of a hand of the individual, and (b) the first set of acceleration readings is captured during the first time period by the accelerometer of the wearable device;

programmatically train the machine learning model, wherein the trained machine learning model (a) generates predictions of eating episodes based at least in part on acceleration readings, and (b) is stored in one or more memory storage areas accessible by the system;

a second set of acceleration readings, wherein (a) the second set of acceleration readings corresponds to motion of the hand of the individual, and (b) the second set of acceleration readings is captured during a second time period by the accelerometer of the wearable device;

generate, using the trained machine learning model and the second set of acceleration readings, a prediction that the second set of acceleration readings indicates a second eating episode; and provide an indication of the prediction that the second set of acceleration readings indicates a second eating episode to the wearable device, wherein the wearable device causes display of at least a portion of the indication.

* * * * *